United States Patent
Sabelle

(10) Patent No.: US 9,585,824 B2
(45) Date of Patent: Mar. 7, 2017

(54) DYE COMPOSITION USING AT LEAST ONE COUPLER OF META-PHENYLENEDIAMINE TYPE SUBSTITUTED IN POSITION 2 IN A MEDIUM COMPRISING A FATTY SUBSTANCE, PROCESSES AND DEVICE

(71) Applicant: L'Oreal, Paris (FR)

(72) Inventor: Stéphane Sabelle, Paris (FR)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 14/764,530

(22) PCT Filed: Jan. 29, 2014

(86) PCT No.: PCT/EP2014/051723
§ 371 (c)(1),
(2) Date: Jul. 29, 2015

(87) PCT Pub. No.: WO2014/118234
PCT Pub. Date: Aug. 7, 2014

(65) Prior Publication Data
US 2015/0374601 A1    Dec. 31, 2015

Related U.S. Application Data

(60) Provisional application No. 61/773,188, filed on Mar. 6, 2013.

(30) Foreign Application Priority Data

Jan. 29, 2013    (FR) .................................... 13 50733

(51) Int. Cl.
| | |
|---|---|
| *A61Q 5/10* | (2006.01) |
| *A61K 8/41* | (2006.01) |
| *A61K 8/31* | (2006.01) |
| *A61K 8/42* | (2006.01) |
| *A61K 8/22* | (2006.01) |
| *A61K 8/46* | (2006.01) |
| *A61K 8/49* | (2006.01) |
| *B65D 81/32* | (2006.01) |

(52) U.S. Cl.
CPC ................ *A61K 8/411* (2013.01); *A61K 8/22* (2013.01); *A61K 8/31* (2013.01); *A61K 8/42* (2013.01); *A61K 8/46* (2013.01); *A61K 8/494* (2013.01); *A61Q 5/10* (2013.01); *B65D 81/32* (2013.01); *A61K 2800/4324* (2013.01); *A61K 2800/882* (2013.01)

(58) Field of Classification Search
CPC . A61Q 5/10; A61K 8/411; A61K 8/42; A61K 8/22; A61K 8/46; A61K 2800/4324; A61K 2800/882; B65D 81/32
USPC ............................................................ 8/405
See application file for complete search history.

(56) References Cited

U.S. PATENT DOCUMENTS

| | | | |
|---|---|---|---|
| 5,015,772 A | 5/1991 | Junino et al. | |
| 5,710,311 A * | 1/1998 | Junino ..................... | A61K 8/46 558/414 |
| 6,024,769 A * | 2/2000 | Cotteret ................. | A61K 8/411 8/408 |
| 2010/0154140 A1* | 6/2010 | Simonet ................... | A61K 8/31 8/416 |

FOREIGN PATENT DOCUMENTS

| | | |
|---|---|---|
| WO | 93/18739 A1 | 9/1993 |
| WO | 2012/146531 A1 | 11/2012 |

OTHER PUBLICATIONS

STIC Search Report dated Jan. 13, 2016.*
International Search Report mailed Sep. 19, 2014, issued in corresponding International Application No. PCT/EP2014/051723, filed Jan. 29, 2014, 2 pages.

* cited by examiner

*Primary Examiner* — Eisa Elhilo
(74) *Attorney, Agent, or Firm* — Christen O'Connor Johnson Kindness PLLC; Llewellyn Lawson; Juan Zheng

(57) ABSTRACT

The present invention relates to a composition for dyeing keratin fibers, in particular human keratin fibers, comprising one or more fatty substances, one or more surfactants, one or more oxidation bases, one or more particular couplers of meta-phenylenediamine type substituted in position 2, and one or more basifying agents, the fatty substance content in the dye composition representing in total at least 5% by weight relative to the total weight of the said composition. The invention also relates to a dyeing process using such a composition, and also to multi-compartment devices suitable for performing the said process.

20 Claims, No Drawings

DYE COMPOSITION USING AT LEAST ONE COUPLER OF META-PHENYLENEDIAMINE TYPE SUBSTITUTED IN POSITION 2 IN A MEDIUM COMPRISING A FATTY SUBSTANCE, PROCESSES AND DEVICE

The present invention relates to a composition for dyeing keratin fibres, in particular human keratin fibres such as the hair, comprising one or more fatty substances, one or more surfactants, one or more oxidation bases, one or more particular couplers of meta-phenylenediamine type substituted in position 2, and one or more basifying agents, the fatty substance content in the dye composition representing in total at least 15% by weight relative to the total weight of the said composition.

The invention also relates to a process for dyeing keratin fibres using the said composition in the presence of one or more chemical oxidizing agents, and also to a multi-compartment device suitable for using the said dye composition.

Many people have sought for a long time to modify the colour of their hair and in particular to mask their grey hair.

It is known practice to dye keratin fibres, and in particular human keratin fibres such as the hair, in order to obtain "permanent" colorations with dye compositions containing oxidation dye precursors, which are generally known as oxidation bases, such as ortho- or para-phenylenediamines, ortho- or para-aminophenols or heterocyclic compounds such as pyrazoles, pyrazolinones or pyrazolopyridines. These oxidation bases are colourless or weakly coloured compounds which, in combination with oxidizing products, can give rise to coloured compounds by an oxidative condensation process.

It is also known that the shades obtained with these oxidation bases may be varied by combining them with couplers or coloration modifiers, the latter being chosen especially from aromatic meta-diamines, meta-aminophenols, meta-diphenols and certain heterocyclic compounds such as indole or pyridine compounds. The variety of molecules used as oxidation bases and couplers allows a wide range of colours to be obtained.

The oxidation dyeing process thus consists in applying to keratin fibres a dye composition comprising oxidation bases or a mixture of oxidation bases and couplers with hydrogen peroxide ($H_2O_2$ or aqueous hydrogen peroxide solution), as oxidizing agent, in leaving it to diffuse, and then in rinsing the fibres.

However, the use of these dye compositions may present a certain number of drawbacks. Specifically, after application to keratin fibres, the dyeing power obtained may not be entirely satisfactory, or even poor, and lead to a restricted range of colours. The colorations may also not be sufficiently remanent with respect to external agents such as light, shampoo or perspiration, and may also be too selective, i.e. the coloration difference is too great along the same keratin fibre that is differently sensitized between its end and its root.

One of the objects of the present invention is especially to propose compositions for dyeing keratin fibres, in particular human keratin fibres such as the hair, which are especially capable of leading to a wide range of colours with colorations that are powerful, sparingly selective and remanent with respect to external agents (such as shampoo, light, perspiration or bad weather).

This aim is achieved by the present invention, one subject of which is especially a composition for dyeing keratin fibres, in particular human keratin fibres such as the hair, comprising:

(i) one or more fatty substances,
(ii) one or more surfactants,
(iii) one or more oxidation bases,
(iv) one or more basifying agents,
(v) one or more meta-phenylenediamine-based couplers of formula (I), and also the addition salts thereof, optical isomers, geometrical isomers and tautomers thereof and/or solvates thereof:

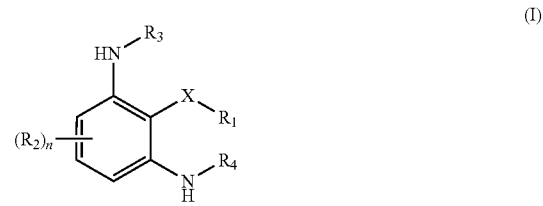

in which formula (I):
  $R_1$ is a linear or branched $C_1$-$C_6$ alkyl radical, which may be substituted with one or more of the following:
    —$CONH_2$ radicals,
    —$NHCOCH_3$ radicals,
    —$NHSO_2CH_3$ radicals,
    di($C_1$-$C_6$)alkylamino radicals,
    hydroxyl radicals,
    amino radicals,
    —COOH radicals,
  $R_2$ represents:
    a hydrogen atom;
    a linear or branched $C_1$-$C_6$ alkyl radical, which may be substituted with one or more of the following:
      —$CONH_2$ radicals,
      —$NHSO_2CH_3$ radicals,
      di($C_1$-$C_6$)alkylamino radicals,
      hydroxyl radicals,
      amino radicals,
      —COOH radicals,
      $C_1$-$C_6$ alkoxy radicals,
    a linear or branched $C_1$-$C_6$ alkoxy radical, which may be substituted with one or more of the following:
      —$CONH_2$ radicals,
      —$NHSO_2CH_3$ radicals,
      di($C_1$-$C_6$)alkylamino radicals,
      hydroxyl radicals,
      amino radicals,
      —COOH radicals,
      $C_1$-$C_6$ alkoxy radicals,
    a halogen radical,
  $R_3$ and $R_4$ represent, independently of each other:
    a hydrogen atom,
    a linear or branched $C_1$-$C_6$ alkyl radical, which may be substituted with one or more of the following:
      di($C_1$-$C_6$)alkylamino radicals,
      hydroxyl radicals,
      amino radicals,
      $C_1$-$C_6$ alkoxy radicals,
  X represents an oxygen or sulfur atom,
  n represents an integer ranging from 0 to 2,
(vi) one or more chemical oxidizing agents,
the fatty substance content representing in total at least 15% by weight relative to the total weight of the said dye composition.

Thus, the couplers used in the dye composition are chosen from the meta-phenylenediamines of formula (I).

The dye compositions make it possible to obtain colorations that are powerful, sparingly selective and remanent with respect to external agents (such as shampoo, light, perspiration or bad weather).

Moreover, the dye compositions according to the present invention allow a wide range of colours to be obtained.

Other subjects, characteristics, aspects and advantages of the present invention will emerge even more clearly on reading the description and the examples that follow.

In the text hereinbelow, and unless otherwise indicated, the limits of a range of values are included in that range.

The expression "at least one" is equivalent to the expression "one or more".

In general, the term "addition salts" of compounds means the addition salts of these compounds with an acid, such as hydrochlorides, hydrobromides, sulfates, citrates, succinates, tartrates, lactates, tosylates, benzenesulfonates, dodecylbenzenesulfonates, phosphates and acetates, and preferably the hydrochlorides, citrates, succinates, tartrates, phosphates and lactates.

The solvates of compounds more particularly represent the hydrates of such compounds and/or the combination of such compounds with a linear or branched $C_1$-$C_4$ alcohol such as methanol, ethanol, isopropanol or n-propanol. Preferably, the solvates are hydrates.

Fatty Substances:

As it has been mentioned, the composition of the invention comprises at least one fatty substance.

The term "fatty substance" means an organic compound that is insoluble in water at ordinary temperature (25° C.) and at atmospheric pressure (760 mmHg or $1.013 \times 10^5$ Pa) (solubility of less than 5%, preferably of less than 1% and even more preferentially of less than 0.1%). They have in their structure at least one hydrocarbon-based chain containing at least 6 carbon atoms or a sequence of at least two siloxane groups. In addition, the fatty substances are generally soluble in organic solvents under the same temperature and pressure conditions, for instance chloroform, dichloromethane, carbon tetrachloride, ethanol, benzene, toluene, tetrahydrofuran (THF), liquid petroleum jelly or decamethylcyclopentasiloxane.

The fatty substances of the invention do not contain salified carboxylic acid groups.

In addition, the fatty substances of the invention are not (poly)oxyalkylenated or (poly)glycerolated ethers.

The term "oil" means a "fatty substance" that is liquid at room temperature (25° C.) and at atmospheric pressure (760 mmHg or $1.013 \times 10^5$ Pa).

The term "non-silicone oil" means an oil not containing any silicon atoms (Si) and the term "silicone oil" means an oil containing at least one silicon atom.

More particularly, the fatty substance(s) are chosen from $C_6$-$C_{16}$ hydrocarbons, hydrocarbons containing more than 16 carbon atoms, non-silicone oils of animal origin, triglycerides of plant or synthetic origin, fluoro oils, fatty alcohols, fatty acid and/or fatty alcohol esters other than triglycerides and non-silicone waxes, in particular plant waxes, non-silicone waxes, and silicones, and mixtures thereof.

It is recalled that the fatty alcohols, esters and acids more particularly have at least one linear or branched, saturated or unsaturated hydrocarbon-based group comprising 6 to 30 and better still from 8 to 30 carbon atoms, which is optionally substituted, in particular with one or more hydroxyl groups (in particular 1 to 4). If they are unsaturated, these compounds can comprise one to three conjugated or non-conjugated carbon-carbon double bonds.

The linear or branched hydrocarbons of mineral or synthetic origin containing more than 16 carbon atoms are preferably chosen from liquid paraffins, petroleum jelly, liquid petroleum jelly, polydecenes and hydrogenated polyisobutene such as Parleam®, and mixtures thereof.

As regards the $C_6$-$C_{16}$ hydrocarbons, they are more particularly linear, branched or optionally cyclic, and are preferably alkanes. Examples that may be mentioned include hexane, cyclohexane, undecane, dodecane, tridecane or isoparaffins, such as isohexadecane, isodecane or isododecane, and mixtures thereof.

As hydrocarbon-based oils of animal origin, mention may be made of perhydrosqualene.

The triglycerides of vegetable or synthetic origin are preferably chosen from liquid fatty acid triglycerides comprising from 6 to 30 carbon atoms, for instance heptanoic or octanoic acid triglycerides, or alternatively, more particularly from those present in plant oils, for instance sunflower oil, corn oil, soybean oil, marrow oil, grapeseed oil, sesame seed oil, hazelnut oil, apricot oil, macadamia oil, arara oil, castor oil, avocado oil, jojoba oil, shea butter oil or synthetic caprylic/capric acid triglycerides, for instance those sold by the company Stéarineries Dubois or those sold under the names Miglyol® 810, 812 and 818 by the company Dynamit Nobel, and mixtures thereof.

Fluoro oils that may be mentioned include perfluoromethylcyclopentane and perfluoro-1,3-dimethylcyclohexane, sold under the names Flutec® PC1 and Flutec® PC3 by the company BNFL Fluorochemicals; perfluoro-1,2-dimethylcyclobutane; perfluoroalkanes such as dodecafluoropentane and tetradecafluorohexane, sold under the names PF 5050® and PF 5060® by the company 3M, or bromoperfluorooctyl sold under the name Foralkyl® by the company Atochem; nonafluoromethoxybutane and nonafluoroethoxyisobutane; perfluoromorpholine derivatives such as 4-trifluoromethyl perfluoromorpholine sold under the name PF 5052® by the company 3M.

The fatty alcohols that are suitable for the implementation of the invention are more particularly chosen from saturated or unsaturated and linear or branched alcohols comprising from 6 to 30 carbon atoms and preferably from 8 to 30 carbon atoms. Examples that may be mentioned include cetyl alcohol, isostearyl alcohol, stearyl alcohol and the mixture thereof (cetylstearyl alcohol), octyldodecanol, 2-butyloctanol, 2-hexyldecanol, 2-undecylpentadecanol, oleyl alcohol, linolenyl alcohol, ricinoleyl alcohol, undecylenyl alcohol and linoleyl alcohol, and mixtures thereof.

As regards the fatty acid and/or fatty alcohol esters other than the triglycerides mentioned above and non-silicone waxes, mention may be made especially of esters of saturated or unsaturated, linear $C_1$-$C_{26}$ or branched $C_3$-$C_{26}$ aliphatic monoacids or polyacids and of saturated or unsaturated, linear $C_1$-$C_{26}$ or branched $C_3$-$C_{26}$ aliphatic monoalcohols or polyalcohols, the total carbon number of the esters being greater than or equal to 6 and more advantageously greater than or equal to 10.

Among the monoesters, mention may be made of dihydroabietyl behenate; octyldodecyl behenate; isocetyl behenate; cetyl lactate; $C_{12}$-$C_{15}$ alkyl lactate; isostearyl lactate; lauryl lactate; linoleyl lactate; oleyl lactate; (iso)stearyl octanoate; isocetyl octanoate; octyl octanoate; cetyl octanoate; decyl oleate; isocetyl isostearate; isocetyl laurate; isocetyl stearate; isodecyl octanoate; isodecyl oleate; isononyl isononanoate; isostearyl palmitate; methyl acetyl ricinoleate; myristyl stearate; octyl isononanoate; 2-ethylhexyl isononate; octyl palmitate; octyl pelargonate; octyl stearate; octyldodecyl erucate; oleyl erucate; ethyl and isopropyl palmitates; 2-ethylhexyl palmitate, 2-octyldecyl palmitate, alkyl myristates such as isopropyl, butyl, cetyl, 2-octyldodecyl, myristyl or stearyl myristate, hexyl stearate, butyl stearate, isobutyl stearate; dioctyl malate, hexyl laurate, 2-hexyldecyl laurate, and mixtures thereof.

Still within the context of this variant, esters of $C_4$-$C_{22}$ dicarboxylic or tricarboxylic acids and of $C_1$-$C_{22}$ alcohols and esters of mono-, di- or tricarboxylic acids and of $C_2$-$C_{26}$ di-, tri-, tetra- or pentahydroxy alcohols may also be used.

Mention may in particular be made of: diethyl sebacate; diisopropyl sebacate; diisopropyl adipate; di(n-propyl) adipate; dioctyl adipate; diisostearyl adipate; dioctyl maleate; glyceryl undecylenate; octyldodecyl stearoyl stearate; pentaerythrityl monoricinoleate; pentaerythrityl tetraisononanoate; pentaerythrityl tetrapelargonate; pentaerythrityl tetraisostearate; pentaerythrityl tetraoctanoate; propylene glycol dicaprylate; propylene glycol dicaprate; tridecyl erucate; triisopropyl citrate; triisostearyl citrate; glyceryl trilactate; glyceryl trioctanoate; trioctyldodecyl citrate; trioleyl citrate; propylene glycol dioctanoate; neopentyl glycol diheptanoate; diethylene glycol diisononanoate; and polyethylene glycol distearates, and mixtures thereof.

Among the esters mentioned above, use is preferably made of ethyl, isopropyl, myristyl, cetyl or stearyl palmitate, 2-ethylhexyl palmitate, 2-octyldecyl palmitate, alkyl myristates, such as isopropyl, butyl, cetyl or 2-octyldodecyl myristate, hexyl stearate, butyl stearate, isobutyl stearate, dioctyl malate, hexyl laurate, 2-hexyldecyl laurate, isononyl isononanoate or cetyl octanoate, and mixtures thereof.

The composition may also comprise, as fatty ester, sugar esters and diesters of $C_6$-$C_{30}$ and preferably $C_{12}$-$C_{22}$ fatty acids. It should be remembered that the term "sugar" means oxygen-comprising hydrocarbon-based compounds bearing several alcohol functions, with or without aldehyde or ketone functions, and which comprise at least 4 carbon atoms. These sugars may be monosaccharides, oligosaccharides or polysaccharides.

Examples of suitable sugars that may be mentioned include sucrose (or saccharose), glucose, galactose, ribose, fucose, maltose, fructose, mannose, arabinose, xylose and lactose, and derivatives thereof, especially alkyl derivatives, such as methyl derivatives, for instance methylglucose.

The sugar esters of fatty acids may be chosen especially from the group comprising the esters or mixtures of esters of sugars described previously and of linear or branched, saturated or unsaturated $C_6$-$C_{30}$ and preferably $C_{12}$-$C_{22}$ fatty acids. If they are unsaturated, these compounds may comprise one to three conjugated or unconjugated carbon-carbon double bonds.

The esters according to this variant can also be chosen from mono-, di-, tri- and tetraesters, polyesters and mixtures thereof.

These esters may be, for example, oleates, laurates, palmitates, myristates, behenates, cocoates, stearates, linoleates, linolenates, caprates, arachidonates or mixtures thereof, such as, in particular, oleate/palmitate, oleate/stearate or palmitate/stearate mixed esters.

More particularly, use is made of monoesters and diesters and in particular mono- or di-oleate, -stearate, -behenate, -oleopalmitate, -linoleate, -linolenate or -oleostearate of sucrose, of glucose or of methylglucose.

An example that may be mentioned is the product sold under the name Glucate® DO by the company Amerchol, which is a methylglucose dioleate.

Examples of esters or mixtures of esters of sugar and of fatty acid that may also be mentioned include:
the products sold under the names F160, F140, F110, F90, F70 and SL40 by the company Crodesta, respectively denoting sucrose palmitate/stearates formed from 73% monoester and 27% diester and triester, from 61% monoester and 39% diester, triester and tetraester, from 52% monoester and 48% diester, triester and tetraester, from 45% monoester and 55% diester, triester and tetraester, from 39% monoester and 61% diester, triester and tetraester, and sucrose mono laurate;
the products sold under the name Ryoto Sugar Esters, for example referenced B370 and corresponding to sucrose behenate formed from 20% monoester and 80% diester-triester-polyester;
the sucrose mono-dipalmitate/stearate sold by the company Goldschmidt under the name Tegosoft® PSE.

The non-silicone wax(es) are especially chosen from carnauba wax, candelilla wax, esparto wax, paraffin wax, ozokerite, plant waxes, such as olive tree wax, rice wax, hydrogenated jojoba wax or absolute flower waxes, such as the blackcurrant blossom essential wax sold by the company Bertin (France), or animal waxes, such as beeswaxes or modified beeswaxes (cerabellina); other waxes or waxy starting materials that may be used according to the invention are in particular marine waxes, such as that sold by the company Sophim under the reference M82, polyethylene waxes or polyolefin waxes in general.

The silicones that may be used in the dye composition of the present invention are volatile or non-volatile, cyclic, linear or branched silicones, which are unmodified or modified by organic groups, having a viscosity from $5\times10^{-6}$ to 2.5 $m^2/s$ at 25° C., and preferably $1\times10^{-5}$ to 1 $m^2/s$.

The silicones that may be used in accordance with the invention may be in the form of oils, waxes, resins or gums.

Preferably, the silicone(s) are chosen from polydialkylsiloxanes, in particular polydimethylsiloxanes (PDMSs), and organomodified polysiloxanes comprising at least one functional group preferably chosen from amino groups and alkoxy groups.

Organopolysiloxanes are defined in greater detail in Walter Noll's *Chemistry and Technology of Silicones* (1968), Academic Press. They may be volatile or non-volatile.

When they are volatile, the silicones are more particularly chosen from those having a boiling point of between 60° C. and 260° C., and even more particularly from:

(i) cyclic polydialkylsiloxanes comprising from 3 to 7 and preferably from 4 to 5 silicon atoms. These are, for example, octamethylcyclotetrasiloxane sold in particular under the name Volatile Silicone® 7207 by Union Carbide or Silbione® 70045 V2 by Rhodia, decamethylcyclopentasiloxane sold under the name Volatile Silicone® 7158 by Union Carbide, and Silbione® 70045 V5 by Rhodia, and mixtures thereof.

Mention may also be made of cyclocopolymers of the dimethylsiloxane/methylalkylsiloxane type, such as Volatile Silicone® FZ 3109 sold by the company Union Carbide, of formula:

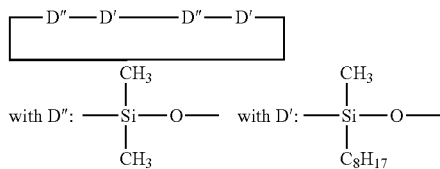

Mention may also be made of mixtures of cyclic polydialkylsiloxanes with organic compounds derived from silicon, such as the mixture of octamethylcyclotetrasiloxane and tetra(trimethylsilyl)pentaerythritol (50/50) and the mixture of octamethylcyclotetrasiloxane and oxy-1,1'-bis(2,2,2', 2',3,3'-hexatrimethylsilyloxy)neopentane;

(ii) linear volatile polydialkylsiloxanes containing 2 to 9 silicon atoms and having a viscosity of less than or equal to $5 \times 10^{-6}$ m$^2$/s at 25° C. An example is decamethyltetrasiloxane sold in particular under the name SH 200 by the company Toray Silicone. Silicones belonging to this category are also described in the article published in Cosmetics and Toiletries, Vol. 91, January 76, pp. 27-32, Todd & Byers, *Volatile Silicone Fluids for Cosmetics*.

Use is preferably made of non-volatile polydialkylsiloxanes, polydialkylsiloxane gums and resins, polyorganosiloxanes modified with the organofunctional groups above, and mixtures thereof.

These silicones are more particularly chosen from polydialkylsiloxanes, among which mention may be made mainly of polydimethylsiloxanes having trimethylsilyl end groups. The viscosity of the silicones is measured at 25° C. according to Standard ASTM 445 Appendix C.

Mention may be made, among these polydialkylsiloxanes, without limitation, of the following commercial products:
- the Silbione® oils of the 47 and 70 047 series or the Mirasil® oils sold by Rhodia, for instance the 70 047 V 500 000 oil;
- the oils of the Mirasil® series sold by the company Rhodia;
- the oils of the 200 series from the company Dow Corning, such as DC200 with a viscosity of 60 000 mm$^2$/s;
- the Viscasil® oils from General Electric and certain oils of the SF series (SF 96, SF 18) from General Electric.

Mention may also be made of polydimethylsiloxanes having dimethylsilanol end groups known under the name dimethiconol (CTFA), such as the oils of the 48 series from the company Rhodia.

In this category of polydialkylsiloxanes, mention may also be made of the products sold under the names Abil Wax® 9800 and 9801 by the company Goldschmidt, which are poly($C_1$-$C_{20}$)dialkylsiloxanes.

The silicone gums that may be used in accordance with the invention are in particular polydialkylsiloxanes and preferably polydimethylsiloxanes with high number-average molecular weights of between 200 000 and 1 000 000, used alone or as a mixture in a solvent. This solvent may be chosen from volatile silicones, polydimethylsiloxane (PDMS) oils, polyphenylmethylsiloxane (PPMS) oils, isoparaffins, polyisobutylenes, methylene chloride, pentane, dodecane and tridecane, or mixtures thereof.

Products that may be used more particularly in accordance with the invention are mixtures such as:
- the mixtures formed from a polydimethylsiloxane hydroxylated at the chain end, or dimethiconol (CTFA), and from a cyclic polydimethylsiloxane, also known as cyclomethicone (CTFA), such as the product Q2 1401 sold by the company Dow Corning;
- the mixtures of a polydimethylsiloxane gum and of a cyclic silicone, such as the product SF 1214 Silicone Fluid from the company General Electric; this product is a gum SF 30 corresponding to a dimethicone, having a number-average molecular weight of 500 000, dissolved in the oil SF 1202 Silicone Fluid corresponding to decamethylcyclopentasiloxane;
- mixtures of two PDMSs with different viscosities, and more particularly of a PDMS gum and a PDMS oil, such as the product SF 1236 from the company General Electric. The product SF 1236 is a mixture of a gum SE 30 defined above with a viscosity of 20 m$^2$/s and of an oil SF 96 with a viscosity of $5 \times 10^{-6}$ m$^2$/s. This product preferably comprises 15% of gum SE 30 and 85% of an oil SF 96.

The organopolysiloxane resins that may be used in accordance with the invention are crosslinked siloxane systems containing the following units:

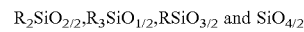

$R_2SiO_{2/2}, R_3SiO_{1/2}, RSiO_{3/2}$ and $SiO_{4/2}$ in which R represents an alkyl containing 1 to 16 carbon atoms. Among these products, those that are particularly preferred are those in which R denotes a $C_1$-$C_4$ lower alkyl group, more particularly methyl.

Mention may be made, among these resins, of the product sold under the name Dow Corning 593 or those sold under the names Silicone Fluid SS 4230 and SS 4267 by the company General Electric, which are silicones of dimethyl/trimethylsiloxane structure.

Mention may also be made of the resins of the trimethylsiloxysilicate type, sold in particular under the names X22-4914, X21-5034 and X21-5037 by the company Shin-Etsu.

The organomodified silicones that may be used in accordance with the invention are silicones as defined above and comprising in their structure one or more organofunctional groups as mentioned previously, attached via a hydrocarbon-based group.

Besides the silicones described above, the organomodified silicones may be polydiarylsiloxanes, especially polydiphenylsiloxanes, and polyalkylarylsiloxanes functionalized with the organofunctional groups mentioned previously.

The polyalkylarylsiloxanes are chosen particularly from linear and/or branched polydimethyl/methylphenylsiloxanes and polydimethyl/diphenylsiloxanes with a viscosity of from $1 \times 10^{-5}$ to $5 \times 10^{-2}$ m$^2$/s at 25° C.

Among these polyalkylarylsiloxanes, examples that may be mentioned include the products sold under the following names:
- the Silbione® oils of the 70 641 series from Rhodia;
- the oils of the Rhodorsil® 70 633 and 763 series from Rhodia;
- the oil Dow Corning 556 Cosmetic Grade Fluid from Dow Corning;
- the silicones of the PK series from Bayer, such as the product PK20;
- the silicones of the PN and PH series from Bayer, such as the products PN1000 and PH1000;
- certain oils of the SF series from General Electric, such as SF 1023, SF 1154, SF 1250 and SF 1265.

Mention may be made, among the organomodified silicones, of polyorganosiloxanes comprising:
- substituted or unsubstituted amino groups, such as the products sold under the name GP 4 Silicone Fluid and GP 7100 by the company Genesee or the products sold under the names Q2 8220 and Dow Corning 929 or 939 by the company Dow Corning. The substituted amino groups are, in particular, $C_1$-$C_4$ aminoalkyl groups;
- alkoxylated groups, such as the product sold under the name Silicone Copolymer F-755 by SWS Silicones, and Abil Wax® 2428, 2434 and 2440 by the company Goldschmidt.

More particularly, the fatty substance(s) are chosen from compounds that are liquid or pasty at room temperature (25° C.) and at atmospheric pressure.

Preferably, the fatty substance(s) are chosen from compounds that are liquid at a temperature of 25° C. and at atmospheric pressure.

The fatty substance(s) are advantageously chosen from hydrocarbons of more than 16 carbon atoms, $C_6$-$C_{16}$ alkanes, oils or triglycerides of plant origin, liquid synthetic triglycerides, fatty alcohols, fatty acid and/or fatty alcohol esters other than triglycerides and non-silicone waxes, non-silicone waxes and silicones, or mixtures thereof.

Preferably, the fatty substance is chosen from liquid petroleum jelly, $C_6$-$C_{16}$ alkanes, polydecenes, liquid fatty acid and/or fatty alcohol esters other than triglycerides, and liquid fatty alcohols, or mixtures thereof.

More preferentially, the fatty substance(s) are chosen from liquid petroleum jelly, $C_6$-$C_{16}$ alkanes, polydecenes and liquid fatty alcohols such as 2-octyldodecanol.

The dye composition according to the invention comprises at least 15% by weight, preferably at least 20% by weight and even more particularly at least 25% by weight of fatty substance, relative to the weight of the dye composition. According to a more particular embodiment, the total amount of fatty substances is at least 30% by weight, particularly at least 40% by weight and even more preferably at least 50% by weight, relative to the total weight of the dye composition.

Preferably, the fatty substance(s) are present in the dye composition according to the invention in a content ranging from 15% to 80% by weight and more preferentially from 20% to 80% by weight relative to the weight of the dye composition. According to a more particular embodiment, the fatty substance content ranges from 25% to 80% by weight, preferably from 30% to 70% by weight and even more advantageously from 30% to 60% by weight relative to the weight of the dye composition. According to an even more preferably embodiment, the fatty substance content ranges from 40% to 60% by weight and even more advantageously from 50% to 60% by weight, relative to the weight of the dye composition.

Surfactants:

As indicated previously, the composition of the invention also comprises one or more surfactants.

In particular, the surfactant(s) are chosen from anionic, amphoteric, zwitterionic, cationic and nonionic surfactants, and preferentially nonionic surfactants.

The term "anionic surfactant" means a surfactant comprising, as ionic or ionizable groups, only anionic groups. These anionic groups are preferably chosen from the groups —C(O)OH, —C(O)O$^-$, —SO$_3$H, —S(O)$_2$O$^-$, —OS(O)$_2$OH, —OS(O)$_2$O$^-$, —P(O)OH$_2$, —P(O)$_2$O$^-$, —P(O)O$_2^-$, —P(OH)$_2$, =P(O)OH, —P(OH)O$^-$, =P(O)O$^-$, =POH and =PO$^-$, the anionic parts comprising a cationic counterion such as those derived from an alkali metal, an alkaline-earth metal, an amine or an ammonium.

As examples of anionic surfactants that may be used in the composition according to the invention, mention may be made of alkyl sulfates, alkyl ether sulfates, alkylamido ether sulfates, alkylaryl polyether sulfates, monoglyceride sulfates, alkylsulfonates, alkylamidesulfonates, alkylarylsulfonates, α-olefin sulfonates, paraffin sulfonates, alkyl sulfosuccinates, alkyl ether sulfosuccinates, alkylamide sulfosuccinates, alkyl sulfoacetates, acylsarcosinates, acylglutamates, alkyl sulfosuccinamates, acylisethionates and N-acyltaurates, polyglycoside polycarboxylic acid and alkyl monoester salts, acyl lactylates, salts of D-galactoside uronic acids, salts of alkyl ether carboxylic acids, salts of alkylaryl ether carboxylic acids, salts of alkylamido ether carboxylic acids; and the corresponding non-salified forms of all these compounds; the alkyl and acyl groups of all these compounds comprising from 6 to 24 carbon atoms and the aryl group denoting a phenyl group.

These compounds can be oxyethylenated and then preferably comprise from 1 to 50 ethylene oxide units.

The salts of $C_6$-$C_{24}$ alkyl monoesters of polyglycoside-polycarboxylic acids can be chosen from $C_6$-$C_{24}$ alkyl polyglycoside-citrates, $C_6$-$C_{24}$ alkyl polyglycoside-tartrates and $C_6$-$C_{24}$ alkyl polyglycoside-sulfo succinates.

When the anionic surfactant(s) are in salt form, it (they) may be chosen from alkali metal salts such as the sodium or potassium salt and preferably the sodium salt, ammonium salts, amine salts and in particular amino alcohol salts or alkaline-earth metal salts such as the magnesium salts.

Examples of amino alcohol salts that may especially be mentioned include monoethanolamine, diethanolamine and triethanolamine salts, monoisopropanolamine, diisopropanolamine and triisopropanolamine salts, and 2-amino-2-methyl-1-propanol, 2-amino-2-methyl-1,3-propanediol and tris(hydroxymethyl)aminomethane salts.

Alkali metal or alkaline-earth metal salts, and in particular sodium or magnesium salts, are preferably used.

Use is preferably made, among the anionic surfactants mentioned, of ($C_6$-$C_{24}$)alkyl sulfates, ($C_6$-$C_{24}$)alkyl ether sulfates comprising from 2 to 50 ethylene oxide units, in particular in the form of alkali metal, ammonium, amino alcohol and alkaline-earth metal salts, or a mixture of these compounds.

In particular, it is preferable to use ($C_{12}$-$C_{20}$)alkyl sulfates, ($C_{12}$-$C_{20}$)alkyl ether sulfates comprising from 2 to 20 ethylene oxide units, in particular in the form of alkali metal, ammonium, amino alcohol and alkaline-earth metal salts, or a mixture of these compounds. Better still, it is preferable to use sodium lauryl ether sulfate containing 2.2 mol of ethylene oxide.

The amphoteric or zwitterionic surfactant(s), which are preferably non-silicone surfactant(s), which may be used in the present invention may especially be derivatives of optionally quaternized secondary or tertiary aliphatic amines, in which derivatives the aliphatic group is a linear or branched chain comprising from 8 to 22 carbon atoms, said amine derivatives containing at least one anionic group, for instance a carboxylate, sulfonate, sulfate, phosphate or phosphonate group. Mention may be made in particular of ($C_8$-$C_{20}$)alkylbetaines, sulfobetaines, ($C_8$-$C_{20}$)alkylamido($C_3$-$C_8$)alkylbetaines and ($C_8$-$C_{20}$)alkylamido($C_6$-$C_8$)alkyl-sulfobetaines.

Among the optionally quaternized secondary or tertiary aliphatic amine derivatives that may be used, as defined above, mention may also be made of the compounds of respective structures (A1) and (A2) below:

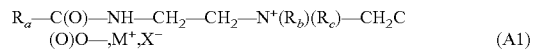

$$R_a\text{—C(O)—NH—CH}_2\text{—CH}_2\text{—N}^+(R_b)(R_c)\text{—CH}_2\text{C(O)O}^-,M^+,X^- \quad (A1)$$

in which formula (A1):

$R_a$ represents a $C_{10}$-$C_{30}$ alkyl or alkenyl group derived from an acid $R_a$COOH preferably present in hydrolysed coconut oil, or a heptyl, nonyl or undecyl group;

$R_b$ represents a β-hydroxyethyl group; and $R_c$ represents a carboxymethyl group;

$M^+$ represents a cationic counterion derived from an alkali metal or alkaline-earth metal, such as sodium, an ammonium ion or an ion derived from an organic amine, and $X^-$ represents an organic or mineral anionic counterion, such as that chosen from halides, acetates, phosphates, nitrates, ($C_1$-$C_4$)alkyl sulfates, ($C_1$-$C_4$)alkyl- or ($C_1$-$C_4$)

alkylaryl sulfonates, in particular methyl sulfate and ethyl sulfate; or alternatively M⁺ and X⁻ are absent;

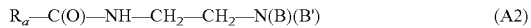

in which formula (A2):

B represents the group —CH₂—CH₂—O—X';

B' represents the group —(CH₂)$_z$Y', with z=1 or 2;

X' represents the group —CH₂—C(O)OH, —CH₂—C(O)OZ', —CH₂—CH₂—C(O)OH, —CH₂—CH₂—C(O)OZ', or a hydrogen atom;

Y' represents the group —C(O)OH, —C(O)OZ', —CH₂—CH(OH)—SO₃H or the group —CH₂—CH(OH)—SO₃—Z';

Z' represents a cationic counterion derived from an alkali metal or alkaline-earth metal, such as sodium, an ammonium ion or an ion derived from an organic amine;

$R_{a'}$ represents a $C_{10}$-$C_{30}$ alkyl or alkenyl group of an acid $R_{a'}$—C(O)OH preferably present in hydrolysed linseed oil or coconut oil, an alkyl group, in particular of $C_{17}$ and its iso form, or an unsaturated $C_{17}$ group.

These compounds are classified in the CTFA dictionary, 5th edition, 1993, under the names disodium cocoamphodiacetate, disodium lauroamphodiacetate, disodium caprylamphodiacetate, disodium caprylamphodiacetate, disodium cocoamphodipropionate, disodium lauroamphodipropionate, disodium caprylamphodipropionate, disodium caprylamphodipropionate, lauroamphodipropionic acid and cocoamphodipropionic acid.

By way of example, mention may be made of the cocoamphodiacetate sold by the company Rhodia under the trade name Miranol® C2M Concentrate.

Use may also be made of the compounds of formula (A3):

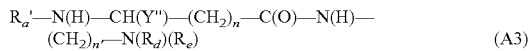

in which formula (A3):

Y" represents the group —C(O)OH, —C(O)OZ", —CH₂—CH(OH)—SO₃H or the group —CH₂—CH(OH)—SO₃—Z";

$R_d$ and $R_e$ represent, independently of each other, a $C_1$-$C_4$ alkyl or hydroxyalkyl radical;

Z" represents a cationic counterion derived from an alkali metal or alkaline-earth metal, such as sodium, an ammonium ion or an ion derived from an organic amine;

$R_a$" represents a $C_{10}$-$C_{30}$ alkyl or alkenyl group derived from an acid $R_a$"—C(O)OH preferably present in coconut oil or in hydrolysed linseed oil;

n and n' denote, independently of each other, an integer ranging from 1 to 3.

Among the compounds of formula (A3), mention may be made of the compound classified in the CTFA dictionary under the name sodium diethylaminopropyl cocoaspartamide and sold by the company Chimex under the name Chimexane HB.

Among the amphoteric or zwitterionic surfactants mentioned above, use is preferably made of ($C_8$-$C_{20}$)alkylbetaines such as cocoylbetaine, and ($C_8$-$C_{20}$)alkylamido($C_3$-$C_8$)alkylbetaines such as cocamidopropylbetaine, and mixtures thereof. More preferentially, the amphoteric or zwitterionic surfactant(s) are chosen from cocamidopropylbetaine and cocoylbetaine.

The cationic surfactant(s) that may be used in the composition according to the invention comprise, for example, optionally polyoxyalkylenated primary, secondary or tertiary fatty amine salts, quaternary ammonium salts, and mixtures thereof.

Examples of quaternary ammonium salts that may in particular be mentioned include:

those corresponding to the general formula (A4) below:

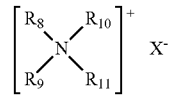

in which formula (A4):

$R_8$ to $R_{11}$, which may be identical or different, represent a linear or branched aliphatic group comprising from 1 to 30 carbon atoms, or an aromatic group such as aryl or alkylaryl, it being understood that at least one of the groups $R_8$ to $R_{11}$ comprises from 8 to 30 carbon atoms and preferably from 12 to 24 carbon atoms; and X⁻ represents an organic or mineral anionic counterion, such as that chosen from halides, acetates, phosphates, nitrates, ($C_1$-$C_4$)alkyl sulfates, ($C_1$-$C_4$)alkyl- or ($C_1$-$C_4$)alkylaryl sulfonates, in particular methyl sulfate and ethyl sulfate.

The aliphatic groups of $R_8$ to $R_{11}$ may also comprise heteroatoms especially such as oxygen, nitrogen, sulfur and halogens.

The aliphatic groups of $R_8$ to $R_{11}$ are chosen, for example, from $C_1$-$C_{30}$ alkyl, $C_1$-$C_{30}$ alkoxy, polyoxy($C_2$-$C_6$)alkylene, $C_1$-$C_{30}$ alkylamide, ($C_{12}$-$C_{22}$)alkylamido($C_2$-$C_6$)alkyl, ($C_{12}$-$C_{22}$)alkyl acetate and $C_1$-$C_{30}$ hydroxyalkyl groups, X⁻ is an anionic counterion chosen from halides, phosphates, acetates, lactates, ($C_1$-$C_4$)alkyl sulfates, ($C_1$-$C_4$)alkyl- or ($C_1$-$C_4$)alkylaryl sulfonates.

Among the quaternary ammonium salts of formula (A4), preference is given firstly to tetraalkylammonium chlorides, for instance dialkyldimethylammonium or alkyltrimethylammonium chlorides in which the alkyl group contains approximately from 12 to 22 carbon atoms, in particular behenyltrimethylammonium chloride, distearyldimethylammonium chloride, cetyltrimethylammonium chloride, benzyldimethylstearylammonium chloride, or else, secondly, distearoylethylhydroxyethylmethylammonium methosulfate, dip almitoylethylhydroxyethylammonium methosulfate or distearoylethylhydroxyethylammonium methosulfate, or else, lastly, palmitylamidopropyltrimethylammonium chloride or stearamidopropyldimethyl(myristyl acetate)ammonium chloride, sold under the name Ceraphyl® 70 by the company Van Dyk;

quaternary ammonium salts of imidazoline, for instance those of formula (A5) below:

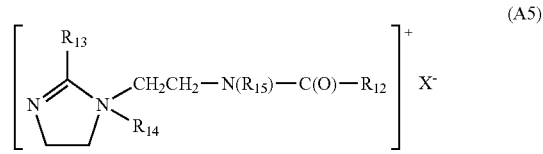

in which formula (A5):

$R_{12}$ represents an alkenyl or alkyl group comprising from 8 to 30 carbon atoms, for example fatty acid derivatives of tallow;

$R_{13}$ represents a hydrogen atom, a $C_1$-$C_4$ alkyl group or an alkenyl or alkyl group comprising from 8 to 30 carbon atoms;

$R_{14}$ represents a $C_1$-$C_4$ alkyl group;

$R_{15}$ represents a hydrogen atom or a $C_1$-$C_4$ alkyl group;

$X^-$ represents an organic or mineral anionic counterion, such as that chosen from halides, phosphates, acetates, lactates, ($C_1$-$C_4$)alkyl sulfates, ($C_1$-$C_4$)alkyl- or ($C_1$-$C_4$)alkylaryl sulfonates.

$R_{12}$ and $R_{13}$ preferably denote a mixture of alkenyl or alkyl groups containing from 12 to 21 carbon atoms, for example fatty acid derivatives of tallow, $R_{14}$ denotes a methyl group, and $R_{15}$ denotes a hydrogen atom. Such a product is sold, for example, under the name Rewoquat® W 75 by the company Rewo;

quaternary diammonium or triammonium salts, particularly of formula (A6) below:

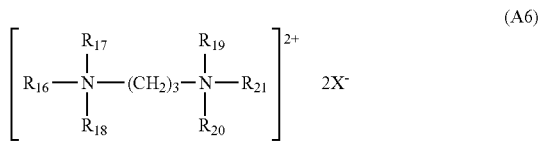

(A6)

in which formula (A6):

$R_{16}$ denotes an alkyl group comprising approximately from 16 to 30 carbon atoms, which is optionally hydroxylated and/or interrupted with one or more oxygen atoms;

$R_{17}$ is chosen from hydrogen, an alkyl group comprising from 1 to 4 carbon atoms or a group —$(CH_2)_3$—$N^+$ $(R_{16a})(R_{17a})(R_{18a})$, X;

$R_{16a}$, $R_{17a}$, $R_{18a}$, $R_{18}$, $R_{19}$, $R_{20}$ and $R_{21}$, which may be identical or different, are chosen from hydrogen and an alkyl group comprising from 1 to 4 carbon atoms; and $X^-$, which may be identical or different, represent an organic or mineral anionic counterion, such as that chosen from halides, acetates, phosphates, nitrates, ($C_1$-$C_4$)alkyl sulfates, ($C_1$-$C_4$)alkyl- or ($C_1$-$C_4$)alkylarylsulfonates, particularly methyl sulfate and ethyl sulfate.

Such compounds are, for example, Finquat CT-P, sold by the company Finetex (Quaternium 89), and Finquat CT, sold by the company Finetex (Quaternium 75);

quaternary ammonium salts containing one or more ester functions, such as those of formula (A7) below:

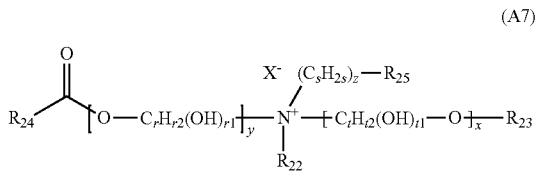

(A7)

in which formula (A7):

$R_{22}$ is chosen from $C_1$-$C_6$ alkyl groups and $C_1$-$C_6$ hydroxyalkyl or $C_1$-$C_6$ dihydroxyalkyl groups;

$R_{23}$ is chosen from:
the group

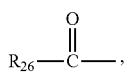

linear or branched, saturated or unsaturated $C_1$-$C_{22}$ hydrocarbon-based groups $R_{27}$,
a hydrogen atom,
$R_{25}$ is chosen from
the group

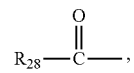

linear or branched, saturated or unsaturated $C_1$-$C_6$ hydrocarbon-based groups $R_{29}$,
a hydrogen atom, $R_{24}$, $R_{26}$ and $R_{28}$, which may be identical or different, are chosen from linear or branched, saturated or unsaturated $C_7$-$C_{21}$ hydrocarbon-based groups;

r, s and t, which may be identical or different, are integers ranging from 2 to 6, r1 and t1, which may be identical or different, are equal to 0 or 1, with r2+r1=2r and t1+t2=2t, y is an integer ranging from 1 to 10, x and z, which may be identical or different, are integers ranging from 0 to 10, $X^-$ represents an organic or mineral anionic counterion, with the proviso that the sum x+y+z is from 1 to 15, that when x is 0 then $R_{23}$ denotes $R_{27}$, and that when z is 0 then $R_{25}$ denotes a linear or branched, saturated or unsaturated $C_1$-$C_6$ hydrocarbon-based radical $R_{29}$.

The alkyl groups $R_{22}$ may be linear or branched, and more particularly linear.

Preferably, $R_{22}$ denotes a methyl, ethyl, hydroxyethyl or dihydroxypropyl group, and more particularly a methyl or ethyl group.

Advantageously, the sum x+y+z is from 1 to 10.

When $R_{23}$ is an $R_{27}$ hydrocarbon-based group, it may be long and may have from 12 to 22 carbon atoms, or may be short and may have from 1 to 3 carbon atoms.

When $R_{25}$ is an $R_{29}$ hydrocarbon-based group, it preferably has 1 to 3 carbon atoms.

Advantageously, $R_{24}$, $R_{26}$ and $R_{28}$, which may be identical or different, are chosen from linear or branched, saturated or unsaturated $C_{11}$-$C_{21}$ hydrocarbon-based groups, and more particularly from linear or branched, saturated or unsaturated $C_{11}$-$C_{21}$ alkyl and alkenyl groups.

Preferably, x and z, which may be identical or different, are equal to 0 or 1.

Advantageously, y is equal to 1.

Preferably, r, s and t, which may be identical or different, are equal to 2 or 3, and even more particularly are equal to 2.

The anionic counterion $X^-$ is preferably a halide, such as chloride, bromide or iodide; a ($C_1$-$C_4$)alkyl sulfate or a ($C_1$-$C_4$)alkyl- or ($C_1$-$C_4$)alkylaryl-sulfonate. However, it is possible to use methanesulfonate, phosphate, nitrate, tosylate, an anion derived from an organic acid, such as acetate or lactate, or any other anion that is compatible with the ammonium comprising an ester function.

The anionic counterion $X^-$ is even more particularly chloride, methyl sulfate or ethyl sulfate.

Use is made more particularly, in the composition according to the invention, of the ammonium salts of formula (A7) in which:

$R_{22}$ denotes a methyl or ethyl group,
x and y are equal to 1,
z is equal to 0 or 1, r, s and t are equal to 2,
$R_{23}$ is chosen from:
the group

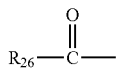

methyl, ethyl or $C_{14}$-$C_{22}$ hydrocarbon-based groups,
a hydrogen atom,
$R_{25}$ is chosen from:
the group

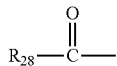

a hydrogen atom,
$R_{24}$, $R_{26}$ and $R_{28}$, which may be identical or different, are chosen from linear or branched, saturated or unsaturated $C_{13}$-$C_{17}$ hydrocarbon-based groups, and preferably from linear or branched, saturated or unsaturated $C_{13}$-$C_{17}$ alkyl and alkenyl groups.

Advantageously, the hydrocarbon radicals are linear.

Among the compounds of formula (A7), examples that may be mentioned include salts, especially the chloride or methyl sulfate, of diacyloxyethyldimethylammonium, diacyloxyethylhydroxyethylmethylammonium, monoacyloxyethyldihydroxyethylmethylammonium, triacyloxyethylmethylammonium or monoacyloxyethylhydroxyethyldimethylammonium, and mixtures thereof. The acyl groups preferably contain from 14 to 18 carbon atoms and originate more particularly from a plant oil, such as palm oil or sunflower oil. When the compound contains several acyl groups, these groups may be identical or different.

These products are obtained, for example, by direct esterification of triethanolamine, triisopropanolamine, an alkyldiethanolamine or an alkyldiisopropanolamine, which are optionally oxyalkylenated, with fatty acids or with mixtures of fatty acids of vegetable or animal origin, or by transesterification of their methyl esters. This esterification is followed by a quaternization by means of an alkylating agent, such as an alkyl halide, preferably methyl or ethyl halide, a dialkyl sulfate, preferably dimethyl or diethyl sulfate, methyl methanesulfonate, methyl para-toluenesulfonate, glycol chlorohydrin or glycerol chlorohydrin.

Such compounds are sold, for example, under the names Dehyquart® by the company Henkel, Stepanquat® by the company Stepan, Noxamium® by the company Ceca or Rewoquat® WE 18 by the company Rewo-Witco.

The composition according to the invention may contain, for example, a mixture of quaternary ammonium salts of monoesters, diesters and triesters with a weight majority of diester salts.

It is also possible to use the ammonium salts containing at least one ester function that are described in U.S. Pat. No. 4,874,554 and U.S. Pat. No. 4,137,180.

Use may be made of behenoylhydroxypropyltrimethylammonium chloride, sold by Kao under the name Quatarmin BTC 131.

Preferably, the ammonium salts containing at least one ester function contain two ester functions.

Among the cationic surfactants that may be present in the composition according to the invention, it is more particularly preferred to choose cetyltrimethylammonium, behenyltrimethylammonium and dipalmitoylethyl-hydroxyethylmethylammonium salts, and mixtures thereof, and more particularly behenyltrimethylammonium chloride, cetyltrimethylammonium chloride and dipalmitoylethylhydroxyethylammonium methosulfate, and mixtures thereof.

Examples of nonionic surfactants that may be used in the composition used according to the invention are described, for example, in the *Handbook of Surfactants* by M. R. Porter, published by Blackie & Son (Glasgow and London), 1991, pp. 116-178.

Examples of oxyalkylenated nonionic surfactants that may be mentioned include:
  oxyalkylenated ($C_8$-$C_{24}$)alkylphenols;
  saturated or unsaturated, linear or branched, oxyalkylenated $C_8$-$C_{30}$ alcohols;
  saturated or unsaturated, linear or branched, oxyalkylenated $C_8$-$C_{30}$ amides;
  esters of saturated or unsaturated, linear or branched, $C_8$-$C_{30}$ acids and of polyethylene glycols;
  polyoxyethylenated esters of saturated or unsaturated, linear or branched, $C_8$-$C_{30}$ acids and of sorbitan;
  fatty acid esters of sucrose;
  ($C_8$-$C_{30}$)alkylpolyglycosides, ($C_8$-$C_{30}$)alkenylpolyglycosides, which are optionally oxyalkylenated (0 to 10 oxyalkylene units) and which comprise 1 to 15 glucose units, ($C_8$-$C_{30}$)alkylglucoside esters;
  saturated or unsaturated, oxyethylenated plant oils;
  condensates of ethylene oxide and/or of propylene oxide, inter alia, alone or as mixtures;
  N—($C_8$-$C_{30}$)alkylglucamine derivatives and N—($C_8$-$C_{30}$)acyl-methylglucamine derivatives;
  aldobionamides;
  amine oxides;
  oxyethylenated and/or oxypropylenated silicones;
  the surfactants contain a number of moles of ethylene oxide and/or of propylene oxide ranging advantageously from 1 to 100, more particularly from 2 to 100, preferably from 2 to 50 and more advantageously from 2 to 30. Advantageously, the nonionic surfactants do not comprise oxypropylene units.

In accordance with a preferred embodiment of the invention, the oxyalkylenated nonionic surfactants are chosen from oxyethylenated $C_8$-$C_{30}$ alcohols comprising from 1 to 100 mol and more particularly from 2 to 100 mol of ethylene oxide; polyoxyethylenated esters of saturated or unsaturated, linear or branched $C_8$-$C_{30}$ acids and of sorbitan comprising from 1 to 100 and better still from 2 to 100 mol of ethylene oxide.

As examples of monoglycerolated or polyglycerolated nonionic surfactants, monoglycerolated or polyglycerolated $C_8$-$C_{40}$ alcohols are preferably used.

In particular, the monoglycerolated or polyglycerolated $C_8$-$C_{40}$ alcohols correspond to formula (A8) below:

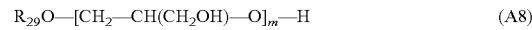

in which formula (A8):
  —$R_{29}$ represents a linear or branched $C_8$-$C_{40}$ and preferably $C_8$-$C_{30}$ alkyl or alkenyl radical; and
  m represents a number ranging from 1 to 30 and preferably from 1 to 10.

As examples of compounds of formula (A8) that are suitable within the context of the invention, mention may be made of lauryl alcohol containing 4 mol of glycerol (INCI name: Polyglyceryl-4 Lauryl Ether), lauryl alcohol containing 1.5 mol of glycerol, oleyl alcohol containing 4 mol of glycerol (INCI name: Polyglyceryl-4 Oleyl Ether), oleyl alcohol containing 2 mol of glycerol (INCI name: Polyglyceryl-2 Oleyl Ether), cetearyl alcohol containing 2 mol of glycerol, cetearyl alcohol containing 6 mol of glycerol, oleocetyl alcohol containing 6 mol of glycerol, and octadecanol containing 6 mol of glycerol.

The alcohol of formula (A8) may represent a mixture of alcohols in the same way that the value of m represents a statistical value, which means that, in a commercial product, several species of polyglycerolated fatty alcohols may coexist in the form of a mixture.

Among the monoglycerolated or polyglycerolated alcohols, it is more particularly preferred to use the $C_8/C_{10}$ alcohol containing 1 mol of glycerol, the $C_{10}/C_{12}$ alcohol containing 1 mol of glycerol and the $C_{12}$ alcohol containing 1.5 mol of glycerol.

Preferably, the surfactant(s) are chosen from nonionic surfactants or from anionic surfactants. More particularly, the surfactant(s) present in the composition are chosen from nonionic surfactants.

Preferentially, the nonionic surfactant used in the process of the invention in the composition is a monooxyalkylenated or polyoxyalkylenated, particularly monooxyethylenated or polyoxyethylenated, or monooxypropylenated or polyoxypropylenated, nonionic surfactant, or a combination thereof, more particularly monooxyethylenated or polyoxyethylenated, monoglycerolated or polyglycerolated surfactants and alkylpolyglucosides.

Even more preferentially, the nonionic surfactants are chosen from polyoxyethylenated sorbitan esters, polyoxyethylenated fatty alcohols and alkylpolyglucosides, and mixtures thereof.

The surfactants may be present in the dye composition according to the invention in a content ranging from 0.1% to 50% by weight and better still from 0.5% to 20% by weight relative to the total weight of the composition.

Oxidation Bases:

The composition of the invention comprises one or more oxidation bases chosen especially from heterocyclic bases and benzene bases, and the addition salts and/or solvates thereof.

The benzene-based oxidation bases according to the invention are particularly chosen from para-phenylenediamines, bis(phenyl)alkylenediamines, para-aminophenols and ortho-aminophenols, and the addition salts and/or solvates thereof.

Among the para-phenylenediamines that may be mentioned, for example, are para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis((β-hydroxyethyl)-para-phenylenediamine, 4-N,N-bis((β-hydroxyethyl)amino-2-methylaniline, 4-N,N-bis((β-hydroxyethyl)amino-2-chloro aniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N-ethyl-N-(β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine, 4-aminophenylpyrrolidine, 2-thienyl-para-phenylenediamine, 2-β-hydroxyethylamino-5-aminotoluene and 3-hydroxy-1-(4'-aminophenyl) pyrrolidine, and the addition salts and/or solvates thereof.

Among the para-phenylenediamines mentioned above, para-phenylenediamine, para-tolylenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine and 2-β-acetylaminoethyloxy-para-phenylenediamine, and the addition salts and/or solvates thereof, are particularly preferred.

Among the bis(phenyl)alkylenediamines, examples that may be mentioned include N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis (β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl) ethylenediamine and 1,8-bis(2,5-diaminophenoxy)-3,6-dioxaoctane, and the addition salts and/or solvates thereof.

Among the para-aminophenols that may be mentioned, for example, are para-aminophenol, 4-amino-3-methylphenol, 4-amino-3-fluorophenol, 4-amino-3-chlorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol and 4-amino-2-fluorophenol, and the addition salts and/or solvates thereof.

Among the ortho-aminophenols, mention may be made, by way of example, of 2-aminophenol, 2-amino-5-methylphenol, 2-amino-6-methylphenol and 5-acetamido-2-aminophenol, and the addition salts and/or solvates thereof.

The heterocyclic bases according to the invention are more particularly chosen from pyridine derivatives, pyrimidine derivatives and pyrazole derivatives, and the addition salts and/or solvates thereof.

Among the pyridine derivatives, mention may be made of the compounds described, for example, in patents GB 1 026 978 and GB 1 153 196, such as 2,5-diaminopyridine, 2-(4-methoxyphenyl)amino-3-aminopyridine, 3,4-diaminopyridine, and the addition salts and/or solvates thereof.

Other pyridine oxidation bases that are useful in the dyeing process according to the invention are the 3-aminopyrazolo[1,5-a]pyridine oxidation bases or the addition salts thereof described, for example, in patent application FR 2 801 308. Examples that may be mentioned include pyrazolo[1,5-a]pyrid-3-ylamine, 2-acetylaminopyrazolo[1,5-a]pyrid-3-ylamine, 2-morpholin-4-ylpyrazolo[1,5-a]pyrid-3-ylamine, 3-aminopyrazolo[1,5-a]pyridine-2-carboxylic acid, 2-methoxypyrazolo[1,5-a]pyrid-3-ylamine, (3-aminopyrazolo[1,5-a]pyrid-7-yl)methanol, 2-(3-aminopyrazolo [1,5-a]pyrid-5-yl)ethanol, 2-(3-aminopyrazolo[1,5-a]pyrid-7-yl)ethanol, (3-aminopyrazolo[1,5-a]pyrid-2-yl)methanol, 3,6-diaminopyrazolo[1,5-a]pyridine, 3,4-diaminopyrazolo [1,5-a]pyridine, pyrazolo[1,5-a]pyridine-3,7-diamine, 7-morpholin-4-ylpyrazolo[1,5-a]pyrid-3-ylamine, pyrazolo [1,5-a]pyridine-3,5-diamine, 5-morpholin-4-ylpyrazolo[1,5-a]pyrid-3-ylamine, 2-[(3-aminopyrazolo[1,5-a]pyrid-5-yl) (2-hydroxyethyl)amino]ethanol, 2-[(3-aminopyrazolo[1,5-a]pyrid-7-yl)(2-hydroxyethyl)amino]ethanol, 3-aminopyrazolo[1,5-a]pyridin-5-ol, 3-aminopyrazolo[1,5- a]pyridin-4-ol, 3-aminopyrazolo[1,5-a]pyridin-6-ol and 3-aminopyrazolo[1,5-a]pyridin-7-ol, and the addition salts and/or solvates thereof.

Mention may be made, among pyrimidine derivatives, of the compounds described, for example, in patents DE 2359399, JP 88-169571, JP 05-63124 and EP 0 770 375 or patent application WO 96/15765, such as 2,4,5,6-tetraaminopyrimidine, 4-hydroxy-2,5,6-triaminopyrimidine, 2-hydroxy-4,5,6-triaminopyrimidine, 2,4-dihydroxy-5,6-diaminopyrimidine, 2,5,6-triaminopyrimidine and the addition salts and/or solvates thereof, and the tautomeric forms thereof, when a tautomeric equilibrium exists.

Among the pyrazole derivatives that may be mentioned are the compounds described in the patents DE 3843892, DE 4133957 and patent applications WO 94/08969, WO 94/08970, FR-A-2 733 749 and DE 195 43 988, such as 4,5-diamino-1-methylpyrazole, 4,5-diamino-1-(β-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-methylaminopyrazole, 3,5-diamino-4-(β-hydroxyethyl)amino-1-methylpyrazole, and the addition salts and/or solvates thereof. Use may also be made of 4,5-diamino-1-(β-methoxyethyl)pyrazole.

Use will preferably be made of a 4,5-diaminopyrazole and even more preferentially of 4,5-diamino-1-(β-hydroxyethyl)pyrazole and/or an addition salt and/or solvate thereof.

Pyrazole derivatives that may also be mentioned include diamino-N,N-dihydropyrazolopyrazolones and especially those described in patent application FR-A-2 886 136, such as the following compounds and the addition salts thereof: 2,3-diamino-6,7-dihydro-1H,5H-pyrazolo[1,2-a]pyrazol-1-one, 2-amino-3-ethylamino-6,7-dihydro-1H,5H-pyrazolo[1,2-a]pyrazol-1-one, 2-amino-3-isopropylamino-6,7-dihydro-1H,5H-pyrazolo[1,2-a]pyrazol-1-one, 2-amino-3-(pyrrolidin-1-yl)-6,7-dihydro-1H,5H-pyrazolo[1,2-a]pyrazol-1-one, 4,5-diamino-1,2-dimethyl-1,2-dihydropyrazol-3-one, 4,5-diamino-1,2-diethyl-1,2-dihydropyrazol-3-one, 4,5-diamino-1,2-di(2-hydroxyethyl)-1,2-dihydropyrazol-3-one, 2-amino-3-(2-hydroxyethyl)amino-6,7-dihydro-1H,5H-pyrazolo[1,2-a]pyrazol-1-one, 2-amino-3-dimethylamino-6,7-dihydro-1H,5H-pyrazolo[1,2-a]pyrazol-1-one, 2,3-diamino-5,6,7,8-tetrahydro-1H,6H-pyridazino[1,2-a]pyrazol-1-one, 4-amino-1,2-diethyl-5-(pyrrolidin-1-yl)-1,2-dihydropyrazol-3-one, 4-amino-5-(3-dimethylaminopyrrolidin-1-yl)-1,2-diethyl-1,2-dihydropyrazol-3-one or 2,3-diamino-6-hydroxy-6,7-dihydro-1H,5H-pyrazolo[1,2-a]pyrazol-1-one and/or an addition salt and/or solvate thereof.

Use will preferably be made of 2,3-diamino-6,7-dihydro-1H,5H-pyrazolo[1,2-a]pyrazol-1-one and/or an addition salt and/or solvate thereof.

Heterocyclic bases that will preferentially be used include 4,5-diamino-1-(β-hydroxyethyl)pyrazole and/or 2,3-diamino-6,7-dihydro-1H,5H-pyrazolo[1,2-a]pyrazol-1-one and/or an addition salt and/or solvate thereof.

Preferably, the oxidation bases are chosen from para-phenylenediamines and heterocyclic bases, and also addition salts and/or solvates thereof, and mixtures thereof.

The oxidation bases used in the composition according to the invention may advantageously represent from 0.0001% to 10% by weight relative to the total weight of the composition, and preferably from 0.005% to 5% by weight relative to the total weight of the dye composition.

Couplers:

As indicated above, the dye composition according to the invention also comprises one or more meta-phenylenediamine-based couplers corresponding to formula (I), and also addition salts thereof, optical isomers, geometrical isomers and tautomers thereof and/or solvates thereof:

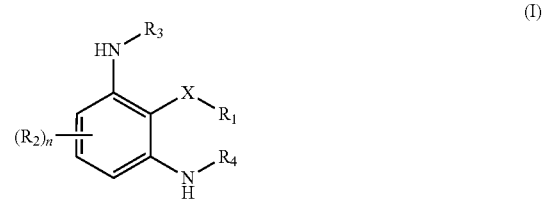

(I)

in which formula (I):
$R_1$ represents a linear or branched $C_1$-$C_6$ alkyl radical, which may be substituted with one or more of the following:
—$CONH_2$ radicals,
—$NHCOCH_3$ radicals,
—$NHSO_2CH_3$ radicals,
di($C_1$-$C_6$)alkylamino radicals,
hydroxyl radicals,
amino radicals,
—COOH radicals,
$R_2$ represents:
a hydrogen atom,
a linear or branched $C_1$-$C_6$ alkyl radical, which may be substituted with one or more of the following:
—$CONH_2$ radicals,
—$NHSO_2CH_3$ radicals,
di($C_1$-$C_6$)alkylamino radicals,
hydroxyl radicals,
amino radicals,
—COOH radicals,
$C_1$-$C_6$ alkoxy radicals,
a linear or branched $C_1$-$C_6$ alkoxy radical, which may be substituted with one or more of the following:
—$CONH_2$ radicals,
—$NHSO_2CH_3$ radicals,
di($C_1$-$C_6$)alkylamino radicals,
hydroxyl radicals,
amino radicals,
—COOH radicals,
$C_1$-$C_6$ alkoxy radicals,
a halogen radical,
$R_3$ and $R_4$ represent, independently of each other:
a hydrogen atom,
a linear or branched $C_1$-$C_6$ alkyl radical, which may be substituted with one or more of the following:
di($C_1$-$C_6$)alkylamino radicals,
hydroxyl radicals,
amino radicals,
$C_1$-$C_6$ alkoxy radicals,
X represents an oxygen or sulfur atom,
n represents an integer ranging from 0 to 2.

According to one embodiment, $R_1$ represents a linear $C_1$-$C_4$ and especially $C_1$ alkyl radical, optionally substituted with one or more hydroxyl groups, an amino group or a group —$NHCOCH_3$.

Preferably, $R_1$ represents an unsubstituted linear $C_1$-$C_4$ and especially $C_1$ alkyl radical.

According to one embodiment, $R_3$ and $R_4$ represent, independently of each other, a hydrogen atom or a linear $C_1$-$C_6$, in particular $C_1$-$C_4$ and more particularly $C_2$ alkyl radical, optionally substituted with a hydroxyl group.

Preferably, $R_3$ represents a hydrogen atom and $R_4$ represents a hydrogen atom or a linear $C_1$-$C_6$, in particular $C_1$-$C_4$ and especially $C_2$ alkyl radical, optionally substituted with a hydroxyl group.

More preferentially, $R_3$ and $R_4$ represent a hydrogen atom.

According to one embodiment, $R_2$ represents a hydrogen atom, a linear $C_1$-$C_4$ and especially $C_1$ alkyl radical or a linear $C_1$-$C_4$ alkoxy radical optionally substituted with a hydroxyl group.

In accordance with one embodiment, X represents an oxygen atom.

According to this embodiment, $R_3$ and $R_4$ preferentially represent, independently of each other, a hydrogen atom or a linear $C_1$-$C_6$, in particular $C_1$-$C_4$ and more particularly $C_2$ alkyl radical, optionally substituted with a hydroxyl group.

In particular, $R_3$ and $R_4$ preferentially represent, in accordance with this embodiment, a hydrogen atom.

In accordance with this embodiment, $R_2$ represents a hydrogen atom, a linear $C_1$-$C_4$ and especially $C_1$ alkyl radical, or a linear $C_1$-$C_4$ alkoxy radical optionally substituted with a hydroxyl group, and $R_3$ and $R_4$ represent, independently of each other, a hydrogen atom or a linear $C_1$-$C_6$, in particular $C_1$-$C_4$ and more particularly $C_2$ alkyl radical, optionally substituted with a hydroxyl group.

According to another embodiment, X represents a sulfur atom.

In accordance with this embodiment, $R_3$ and $R_4$ preferentially represent a hydrogen atom.

According to this embodiment, $R_3$ and $R_4$ preferentially represent a hydrogen atom and $R_1$ represents a linear $C_1$-$C_4$ and especially $C_1$ alkyl radical, optionally substituted with one or more hydroxyl groups, an amino group or a group —$NHCOCH_3$.

Preferably, the meta-phenylenediamine-based coupler(s) corresponding to formula (I) are chosen from the following compounds, and also the addition salts thereof, optical isomers, geometrical isomers and tautomers thereof, and/or solvates thereof:

(1)

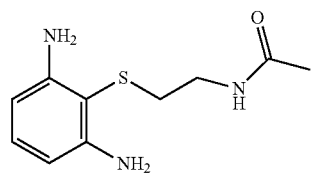

N-[2-(2,6-diaminophenylsulfanyl)ethyl]
acetamide

-continued (2)

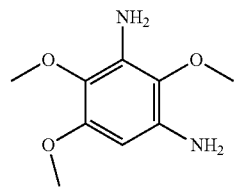

2,4,5-trimethoxybenzene-
1,3-diamine (3)

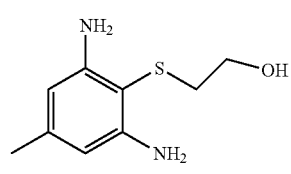

2-(2,6-diamino-4-
methylphenylsulfanyl)ethanol (4)

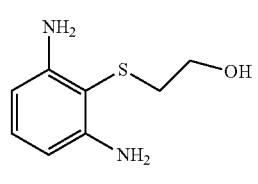

2-(2,6-diaminophenylsulfanyl)
ethanol (5)

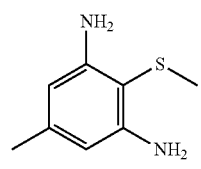

5-methyl-2-methylsulfanyl
benzene-1,3-diamine (6)

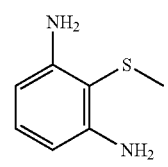

2-methylsulfanyl
benzene-1,3-diamine (7)

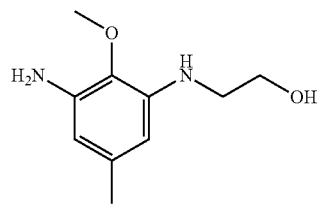

2-(3-amino-2-methoxy-5-
methylphenylamino)ethanol

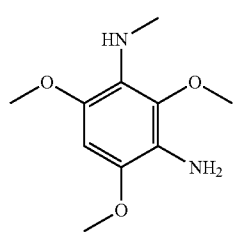

2,4,6-trimethoxy-N-methylbenzene-1,3-diamine (8)

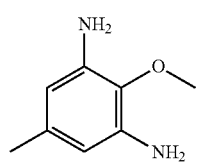

2-methoxy-5-methyl benzene-1,3-diamine (9)

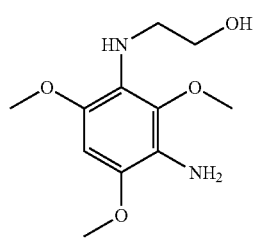

2-(3-amino-2,4,6-trimethoxyphenylamino)ethanol (10)

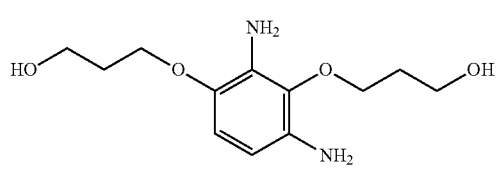

3-[2,6-diamino-3-(3-hydroxypropoxy)phenoxy]propan-1-ol (11)

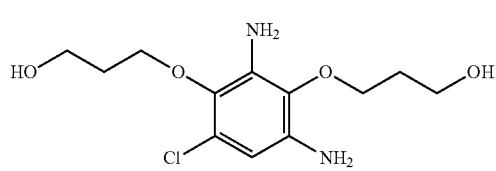

3-[2,6-diamino-4-chloro-3-(3-hydroxypropoxy)phenoxy]propan-1-ol (12)

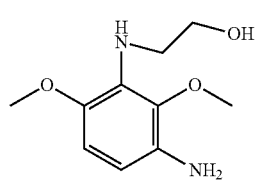

2-(3-amino-2,6-dimethoxyphenylamino)ethanol (13)

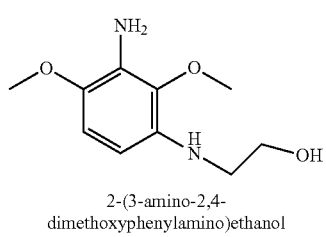

2-(3-amino-2,4-dimethoxyphenylamino)ethanol (14)

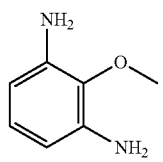

2-methoxybenzene-1,3-diamine (15)

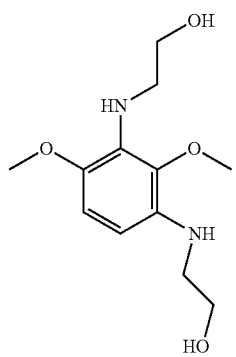

2-[3-(2-hydroxyethylamino)-2,6-dimethoxyphenylamino]ethanol (16)

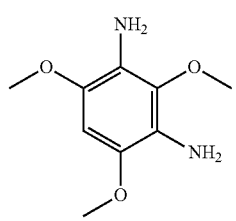

2,4,6-trimethoxybenzene-1,3-diamine (17)

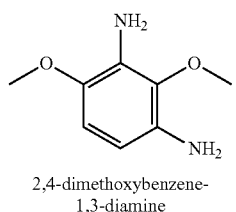

2,4-dimethoxybenzene-1,3-diamine (18)

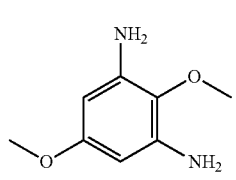

2,5-dimethoxybenzene-1,3-diamine (19)

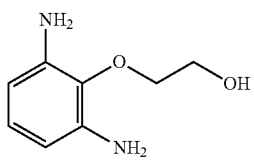

2-(2,6-diaminophenoxy)ethanol

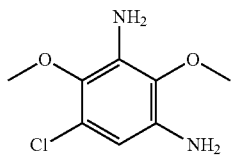

5-chloro-2,4-dimethoxy-
benzene-1,3-diamine

More preferentially, the couplers used according to the present invention are chosen from couplers (1) and (2), and also the addition salts thereof, optical isomers, geometrical isomers and tautomers thereof, and/or solvates thereof.

According to one embodiment, the dye composition according to the invention comprises:

(i) one or more fatty substances,
(ii) one or more surfactants,
(iii) one or more oxidation bases chosen from para-phenylenediamines and heterocyclic bases, and also addition salts and/or solvates thereof, and mixtures thereof,
(iv) one or more basifying agents,
(v) one or more couplers corresponding to formula (I) chosen from couplers (1) and (2), and also the addition salts thereof, optical isomers, geometrical isomers and tautomers thereof, and/or solvates thereof,
(vi) one or more chemical oxidizing agents, the fatty substance content representing in total at least 15% by weight relative to the total weight of the said dye composition.

The meta-phenylenediamine-based coupler(s) of formula (I) may be present in the dye composition according to the invention in a content ranging from 0.0001% to 10% by weight and preferably from 0.005% to 5% by weight relative to the total weight of the dye composition.

Basifying Agents:

As indicated previously, the dye composition according to the invention also comprises one or more basifying agents.

The basifying agent(s) may be mineral or organic or hybrid.

The mineral basifying agent(s) are preferably chosen from aqueous ammonia, alkali metal carbonates or bicarbonates such as sodium carbonate, potassium carbonate, sodium bicarbonate or potassium bicarbonate, sodium hydroxide or potassium hydroxide, or mixtures thereof.

The organic basifying agent(s) are preferably chosen from organic amines with a $pK_b$ at 25° C. of less than 12, preferably less than 10 and even more advantageously less than 6. It should be noted that it is the $pK_b$ corresponding to the function of highest basicity. In addition, the organic amines do not comprise an alkyl or alkenyl fatty chain comprising more than ten carbon atoms.

The organic basifying agent(s) are chosen, for example, from alkanolamines, oxyethylenated and/or oxypropylenated ethylenediamines, amino acids and the compounds of formula (II) below:

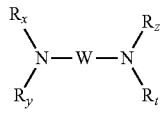

in which formula (II) W is a divalent $C_1$-$C_6$ alkylene radical optionally substituted with one or more hydroxyl groups or a $C_1$-$C_6$ alkyl radical, and/or optionally interrupted with one or more heteroatoms such as O, or $NR_u$, $R_x$, $R_y$, $R_z$, $R_t$ and $R_u$, which may be identical or different, represent a hydrogen atom or a $C_1$-$C_6$ alkyl, $C_1$-$C_6$ hydroxyalkyl or $C_1$-$C_6$ aminoalkyl radical.

Examples of amines of formula (II) that may be mentioned include 1,3-diaminopropane, 1,3-diamino-2-propanol, spermine and spermidine.

The term "alkanolamine" means an organic amine comprising a primary, secondary or tertiary amine function, and one or more linear or branched $C_1$-$C_8$ alkyl groups bearing one or more hydroxyl radicals.

The organic amines chosen from alkanolamines such as monoalkanolamines, dialkanolamines or trialkanolamines, comprising one to three identical or different $C_1$-$C_4$ hydroxyalkyl radicals are in particular suitable for carrying out the invention.

Among compounds of this type, mention may be made of monoethanolamine (MEA), diethanolamine, triethanolamine, mono isopropanolamine, diisopropanolamine, N-dimethylaminoethanolamine, 2-amino-2-methyl-1-propanol, triisopropanolamine, 2-amino-2-methyl-1,3-propanediol, 3-amino-1,2-propanediol, 3-dimethylamino-1,2-propanediol and tris(hydroxymethylamino)methane.

More particularly, the amino acids that may be used are of natural or synthetic origin, in their L, D or racemic form, and comprise at least one acid function chosen more particularly from carboxylic acid, sulfonic acid, phosphonic acid or phosphoric acid functions. The amino acids may be in neutral or ionic form.

As amino acids that may be used in the present invention, mention may be made especially of aspartic acid, glutamic acid, alanine, arginine, ornithine, citrulline, asparagine, carnitine, cysteine, glutamine, glycine, histidine, lysine, isoleucine, leucine, methionine, N-phenylalanine, proline, serine, taurine, threonine, tryptophan, tyrosine and valine.

Advantageously, the amino acids are basic amino acids comprising an additional amine function optionally included in a ring or in a ureido function.

Such basic amino acids are preferably chosen from those corresponding to formula (III) below, and also salts thereof:

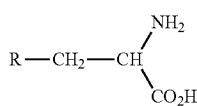

in which formula (III), R represents a group chosen from:

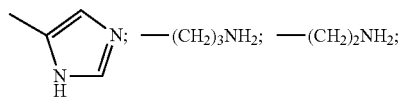

-continued

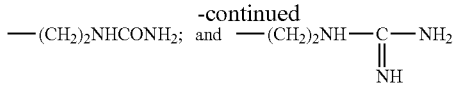

The compounds corresponding to formula (III) are histidine, lysine, arginine, ornithine and citrulline.

The organic amine may also be chosen from organic amines of heterocyclic type. Besides histidine that has already been mentioned in the amino acids, mention may in particular be made of pyridine, piperidine, imidazole, triazole, tetrazole and benzimidazole.

The organic amine may also be chosen from amino acid dipeptides. As amino acid dipeptides that may be used in the present invention, mention may in particular be made of carnosine, anserine and balenine.

The organic amine may also be chosen from compounds comprising a guanidine function. As amines of this type that may be used in the present invention, besides arginine, which has already been mentioned as an amino acid, mention may be made especially of creatine, creatinine, 1,1-dimethylguanidine, 1,1-diethylguanidine, glycocyamine, metformin, agmatine, N-amidino alanine, 3-guanidinopropionic acid, 4-guanidinobutyric acid and 2-([amino(imino)methyl]amino)ethane-1-sulfonic acid.

Hybrid compounds that may be mentioned include the salts of the amines mentioned previously with acids such as carbonic acid or hydrochloric acid.

Use may in particular be made of guanidine carbonate or monoethanolamine hydrochloride.

Preferably, the basifying agent(s) present in the composition of the invention are chosen from alkanolamines, amino acids in neutral or ionic form, in particular basic amino acids, and preferably corresponding to those of the formula (III). Even more preferentially, the basifying agent(s) are chosen from monoethanolamine (MEA) and basic amino acids in neutral or ionic form.

Advantageously, the composition according to the invention has a content of basifying agent(s) ranging from 0.01% to 30% by weight and preferably from 0.1% to 20% by weight relative to the weight of the composition.

According to a first particular embodiment, the composition according to the invention, or the process according to the invention, does not use aqueous ammonia, or a salt thereof, as basifying agent.

According to a second embodiment, if the composition or the process according to the invention were to use aqueous ammonia, or a salt thereof, as basifying agent, its content advantageously would not exceed 0.03% by weight (expressed as $NH_3$) and preferably would not exceed 0.01% by weight, relative to the weight of the composition of the invention.

Preferably, if the composition comprises aqueous ammonia, or a salt thereof, then the weight amount of basifying agent(s) other than the aqueous ammonia is greater than that of the aqueous ammonia (expressed as $NH_3$).

Chemical Oxidizing Agent:

The dye composition of the invention also comprises one or more chemical oxidizing agents.

The term "chemical oxidizing agent" means an oxidizing agent other than atmospheric oxygen. More particularly, the chemical oxidizing agent(s) are chosen from hydrogen peroxide, urea peroxide, alkali metal bromates, peroxygenated salts, for instance persulfates, perborates, peracids and precursors thereof and percarbonates of alkali metals or alkaline-earth metals.

This oxidizing agent advantageously consists of hydrogen peroxide especially as an aqueous solution (aqueous hydrogen peroxide solution), the concentration of which may range more particularly from 0.1% to 50% by weight, even more preferentially from 0.5% to 20% by weight and better still from 1% to 15% by weight, relative to the weight of the composition.

Preferably, the composition of the invention does not contain any peroxygenated salts.

Additional Couplers

The dye composition according to the present invention may also contain one or more additional couplers other than the meta-phenylenediamine-based couplers of formula (I) as described previously.

Among these additional couplers, mention may be made especially of meta-phenylenediamines, meta-aminophenols, meta-diphenols, naphthalene-based couplers and heterocyclic couplers, and also the addition salts thereof and/or solvates thereof.

Examples that may be mentioned include 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, 3-ureidoaniline, 3-ureido-1-(dimethylamino)benzene, sesamol, 1-β-hydroxyethylamino-3,4-methylenedioxybenzene, α-naphthol, 2-methyl-1-naphthol, 6-hydroxyindole, 4-hydroxyindole, 4-hydroxy-N-methylindole, 2-amino-3-hydroxypyridine, 6-hydroxybenzomorpholine, 3,5-diamino-2,6-dimethoxypyridine, 1-N-(β-hydroxyethyl)amino-3,4-methylenedioxybenzene, 2,6-bis(β-hydroxyethylamino)toluene, 6-hydroxyindoline, 2,6-dihydroxy-4-methylpyridine, 1H-3-methylpyrazol-5-one, 1-phenyl-3-methylpyrazol-5-one, 2,6-dimethylpyrazolo[1,5-b][1,2,4]triazole, 2,6-dimethyl[3,2-c][1,2,4]triazole and 6-methylpyrazolo[1,5-a]benzimidazole, and mixtures thereof.

The additional coupler(s) each advantageously represent from 0.0001% to 10% by weight, relative to the total weight of the composition, and preferably from 0.005% to 5% by weight, relative to the total weight of the composition of the invention.

Additional Dyes

The dye composition according to the present invention may also contain one or more direct dyes.

The latter are more particularly chosen from ionic or nonionic species, preferably cationic or nonionic species. These direct dyes may be synthetic or of natural origin.

Examples of suitable direct dyes that may be mentioned include azo direct dyes; methine direct dyes; carbonyl direct dyes; azine direct dyes; nitro(hetero)aryl direct dyes; tri(hetero)arylmethane direct dyes; porphyrin direct dyes; phthalocyanine direct dyes, and natural direct dyes, alone or as mixtures.

More particularly, the azo dyes comprise an —N═N— function, the two nitrogen atoms of which do not simultaneously participate in a ring. However, it is not excluded for one of the two nitrogen atoms of the sequence —N═N— to be a engaged in a ring.

The dyes of the methine family are more particularly compounds comprising at least one sequence chosen from >C═C< and —N═C< in which the two atoms do not simultaneously participate in a ring. However, it is pointed out that one of the nitrogen or carbon atoms of the sequences may be engaged in a ring. More particularly, the dyes of this family are derived from compounds of the type such as methines, azomethines, monoarylmethanes and diarylmethanes, indoamines (or diphenylamines), indophenols, indoanilines, carbocyanines, azacarbocyanines and isomers thereof, diazacarbocyanines and isomers thereof, tetraazacarbocyanines and hemicyanines.

As regards the dyes of the carbonyl family, examples that may be mentioned include dyes chosen from acridone, benzoquinone, anthraquinone, naphthoquinone, benzanthrone, anthranthrone, pyranthrone, pyrazolanthrone, pyrimidinoanthrone, flavanthrone, idanthrone, flavone, (iso) violanthrone, isoindolinone, benzimidazolone, isoquinolinone, anthrapyridone, pyrazoloquinazolone, perinone, quinacridone, quinophthalone, indigoid, thio indigo, naphthalimide, anthrapyrimidine, diketopyrrolopyrrole and coumarin.

As regards the dyes of the cyclic azine family, mention may be made especially of azine, xanthene, thioxanthene, fluorindine, acridine, (di)oxazine, (di)thiazine and pyronin.

The nitro(hetero)aromatic dyes are more particularly nitrobenzene or nitropyridine direct dyes.

As regards the dyes of porphyrin or phthalocyanine type, it is possible to use cationic or non-cationic compounds, optionally comprising one or more metals or metal ions, for instance alkali metals, alkaline-earth metals, zinc and silicon.

Examples of particularly suitable direct dyes that may be mentioned include nitrobenzene dyes; azo direct dyes; azomethine direct dyes; methine direct dyes; azacarbocyanine direct dyes, for instance tetraazacarbocyanines (tetraazapentamethines); quinone and in particular anthraquinone, naphthoquinone or benzoquinone direct dyes; azine direct dyes; xanthene direct dyes; triarylmethane direct dyes; indoamine direct dyes; indigoid direct dyes; phthalocyanine direct dyes, porphyrin direct dyes and natural direct dyes, alone or as mixtures.

Among the natural direct dyes that may be used according to the invention, mention may be made of lawsone, juglone, alizarin, purpurin, carminic acid, kermesic acid, purpurogallin, protocatechaldehyde, indigo, isatin, curcumin, spinulo sin, apigenidin and orceins. Use may also be made of extracts or decoctions comprising these natural dyes and in particular henna-based poultices or extracts.

When they are present, the direct dye(s) more particularly represent from 0.0001% to 10% by weight and preferably from 0.005% to 5% by weight relative to the total weight of the composition.

Solvent:

The dye composition may also comprise one or more organic solvents.

Examples of organic solvents that may be mentioned include linear or branched $C_2$-$C_4$ alkanols, such as ethanol and isopropanol; glycerol; polyols and polyol ethers, for instance 2-butoxyethanol, propylene glycol, dipropylene glycol, propylene glycol monomethyl ether, diethylene glycol monomethyl ether and monoethyl ether, and also aromatic alcohols or ethers, for instance benzyl alcohol or phenoxyethanol, and mixtures thereof.

The organic solvent(s), if they are present, represent a content usually ranging from 1% to 40% by weight and preferably from 5% to 30% by weight relative to the weight of the composition.

Other Additives:

The composition according to the invention may also contain various adjuvants conventionally used in hair dye compositions, such as anionic, cationic, nonionic, amphoteric or zwitterionic polymers or mixtures thereof; mineral thickeners, and in particular fillers such as clays or talc; organic thickeners with, in particular, anionic, cationic, nonionic and amphoteric polymeric associative thickeners; antioxidants; penetrants; sequestrants; fragrances; dispersants; film-forming agents; ceramides; preserving agents; opacifiers.

The above adjuvants are generally present in an amount, for each of them, of between 0.01% and 20% by weight relative to the weight of the composition.

The composition may especially comprise one or more mineral thickeners chosen from organophilic clays and fumed silicas, or mixtures thereof.

The organophilic clay may be chosen from montmorillonite, bentonite, hectorite, attapulgite and sepiolite, and mixtures thereof. The clay is preferably a bentonite or a hectorite.

These clays may be modified with a chemical compound chosen from quaternary amines, tertiary amines, amine acetates, imidazolines, amine soaps, fatty sulfates, alkylarylsulfonates and amine oxides, and mixtures thereof.

Mention may be made, as organophilic clays, of quaternium-18 bentonites, such as those sold under the names Bentone 3, Bentone 38 and Bentone 38V by the company Rheox, Tixogel VP by the company United Catalyst and Claytone 34, Claytone 40 and Claytone XL by the company Southern Clay; stearalkonium bentonites, such as those sold under the names Bentone 27 by the company Rheox, Tixogel LG by the company United Catalyst and Claytone AF and Claytone APA by the company Southern Clay; and quaternium-18/benzalkonium bentonite, such as those sold under the names Claytone HT and Claytone PS by the company Southern Clay.

The fumed silicas may be obtained by high-temperature hydrolysis of a volatile silicon compound in an oxyhydrogen flame, producing a finely divided silica. This process makes it possible especially to obtain hydrophilic silicas bearing a large number of silanol groups at their surface. Such hydrophilic silicas are sold, for example, under the names Aerosil 130®, Aerosil 200®, Aerosil 255®, Aerosil 300® and Aerosil 380® by the company Degussa and Cab-O-Sil HS-5®, Cab-O-Sil EH-5®, Cab-O-Sil LM-130®, Cab-O-Sil MS-55® and Cab-O-Sil M-5® by the company Cabot.

It is possible to chemically modify the surface of the silica by chemical reaction for the purpose of reducing the number of silanol groups. It is especially possible to replace silanol groups with hydrophobic groups: a hydrophobic silica is then obtained.

The hydrophobic groups may be:
trimethylsiloxyl groups, which are obtained in particular by treating fumed silica in the presence of hexamethyldisilazane. Silicas thus treated are known as "Silica silylate" according to the CTFA (6th Edition, 1995). They are sold, for example, under the references Aerosil R812® by the company Degussa and Cab-O-Sil TS-530® by the company Cabot,
dimethylsilyloxyl or polydimethylsiloxane groups, which are obtained in particular by treating fumed silica in the presence of polydimethylsiloxane or dimethyldichlorosilane. Silicas thus treated are known as "Silica dimethyl silylate" according to the CTFA (6th edition, 1995). They are sold, for example, under the references Aerosil R972® and Aerosil R974® by the company Degussa and Cab-O-Sil TS-610® and Cab-O-Sil TS-720® by the company Cabot.

The fumed silica preferably has a particle size that may be nanometric to micrometric, for example ranging from about 5 to 200 nm.

Preferably, the composition comprises a hectorite, an organomodified bentonite or an optionally modified fumed silica.

When it is present, the mineral thickener represents from 1% to 30% by weight relative to the weight of the composition.

The composition may also comprise one or more organic thickeners.

These thickeners may be chosen from fatty acid amides (coconut acid diethanolamide or monoethanolamide, oxyethylenated alkyl ether carboxylic acid monoethanolamide), polymeric thickeners, such as cellulose-based thickeners (hydroxyethylcellulose, hydroxypropylcellulose, carboxymethylcellulose), guar gum and derivatives thereof (hydroxypropyl guar), gums of microbial origin (xanthan gum, scleroglucan gum), crosslinked homopolymers of acrylic acid or of acrylamidopropanesulfonic acid and associative polymers (polymers comprising hydrophilic regions and hydrophobic regions having a fatty chain (alkyl or alkenyl chain comprising at least 10 carbon atoms) which are capable, in an aqueous medium, of reversibly associating with each other or with other molecules).

According to a specific embodiment, the organic thickener is chosen from cellulose-based thickeners (hydroxyethylcellulose, hydroxypropylcellulose, carboxymethylcellulose), guar gum and derivatives thereof (hydroxypropyl guar), gums of microbial origin (xanthan gum, scleroglucan gum) and crosslinked homopolymers of acrylic acid or of acrylamidopropanesulfonic acid, and preferably from cellulose-based thickeners with in particular hydroxyethylcellulose.

The content of organic thickener(s), if they are present, usually ranges from 0.01% to 20% by weight and preferably from 0.1% to 5% by weight, relative to the weight of the composition.

The composition of the invention can be provided in various forms, for instance a solution, an emulsion (milk or cream) or a gel.

According to a preferred embodiment, the dye composition according to the invention comprises:

(i) one or more non-silicone fatty substances which are liquid at a temperature of 25° C. and at atmospheric pressure, and which do not contain any $C_2$-$C_3$ (poly)oxyalkylene units or any (poly)glycerol units, (ii) one or more surfactants chosen from nonionic surfactants, (iii) one or more oxidation bases chosen especially from heterocyclic bases and benzene-based bases, and addition salts thereof and/or solvates thereof, (iv) one or more basifying agents chosen from alkanolamines and amino acids in neutral or ionic form, or mixtures thereof, (v) one or more meta-phenylenediamine-based couplers of formula (I) as described previously, (vi) one or more chemical oxidizing agents, the fatty substance content representing in total at least 15% by weight, advantageously at least 20% by weight and preferably at least 25% by weight of fatty substance, relative to the total weight of the said dye composition. According to a more particular embodiment, the fatty substance content represents in total at least 30% by weight, particularly at least 40% by weight and even more preferably at least 50% by weight, relative to the total weight of the said dye composition.

Preferably, the dye composition according to the present invention comprises:

(i) one or more non-silicone fatty substances, which are liquid at a temperature of 25° C. and at atmospheric pressure, and which do not contain any $C_2$-$C_3$ (poly)oxyalkylene units or any (poly)glycerol units, chosen from liquid petroleum jelly, liquid esters of fatty acids and/or of fatty alcohols other than triglycerides, and liquid fatty alcohols, or mixtures thereof, (ii) one or more surfactants chosen from nonionic surfactants, (iii) one or more oxidation bases chosen from heterocyclic bases, para-phenylenediamines, bis(phenyl)alkylenediamines, para-aminophenols and ortho-aminophenols, and addition salts thereof and/or solvates thereof, (iv) one or more basifying agents chosen from alkanolamines and basic amino acids of formula (III), or mixtures thereof, (v) one or more meta-phenylenediamine-based couplers of formula (I) as described previously, in which:
X represents an oxygen atom,
$R_1$ represents a linear $C_1$-$C_4$ and especially $C_1$ alkyl radical, optionally substituted with one or more hydroxyl groups, an amino group or a group —NHCOCH$_3$,
$R_3$ and $R_4$ represent, independently of each other, a hydrogen atom or a linear $C_1$-$C_6$, in particular $C_1$-$C_4$ and more particularly $C_2$ alkyl radical, optionally substituted with a hydroxyl group,
$R_2$ represents a hydrogen atom, a linear $C_1$-$C_4$ and especially $C_1$ alkyl radical or a linear $C_1$-$C_4$ alkoxy radical optionally substituted with a hydroxyl group,
n is an integer ranging from 0 to 2, (vi) one or more chemical oxidizing agents, the fatty substance content representing in total at least 15% by weight, advantageously at least 20% by weight and preferably at least 25% by weight of fatty substance, relative to the total weight of the said dye composition, and, in accordance with a more particular embodiment, the fatty substance content is not more than 80% by weight, and preferably the said content ranges from 30% to 70% by weight and more advantageously from 30% to 60% by weight relative to the weight of the dye composition. According to a more preferably embodiment, the fatty substance content represents in total at least 30% by weight, particularly at least 40% by weight and even more preferably at least 50% by weight, relative to the total weight of the said dye composition and preferably the said content ranges from 40% to 60% by weight and advantageously from 50% to 60% by weight, relative to the weight of the dye composition.

More preferentially, the dye composition according to the present invention comprises:

(i) one or more non-silicone fatty substances, which are liquid at a temperature of 25° C. and at atmospheric pressure, and which do not contain any $C_2$-$C_3$ (poly)oxyalkylene units or any (poly)glycerol units, chosen from liquid petroleum jelly, liquid esters of fatty acids and/or of fatty alcohols, and liquid fatty alcohols, or mixtures thereof, (ii) one or more surfactants chosen from nonionic surfactants chosen from monooxyalkylene and polyoxyalkylene, especially polyoxyethylene, nonionic surfactants, and optionally oxyethylenated alkylpolyglucosides, (iii) one or more oxidation bases chosen from heterocyclic bases, para-phenylenediamines, bis(phenyl)alkylenediamines, para-aminophenols and ortho-aminophenols, and addition salts thereof and/or solvates thereof, (iv) one or more basifying agents chosen from alkanolamines, in particular monoethanolamine, and basic amino acids of formula (III), or mixtures thereof, (v) one or more meta-phenylenediamine-based couplers of formula (I) chosen from couplers (1) and (2), and also the addition salts thereof, optical isomers, geometrical isomers and tautomers thereof, and/or solvates thereof, (vi) hydrogen peroxide as chemical oxidizing agent, especially an aqueous hydrogen peroxide solution, the fatty substance content representing in total at least 15% by weight, advantageously at least 20% by weight and preferably at least 25% by weight of fatty substance, relative to the total weight of the said dye composition, and, in accordance with a more particular embodiment, the fatty substance content is not more than 80% by weight, and preferably the said content ranges from 30% to 70% by weight and more advantageously from 30% to 60% by weight relative to the weight of the dye composition. According to a more preferably embodiment, the fatty substance content represents in total at least 30% by weight, particularly at least 40% by weight and even more preferably at least 50% by weight, relative to the total weight of the said dye composition and preferably the said content ranges from 40% to 60% by weight and advantageously from 50% to 60% by weight, relative to the weight of the dye composition.

PROCESSES OF THE INVENTION

The process for dyeing keratin fibres, in particular human keratin fibres such as the hair, consists in applying to the said fibres a composition as defined previously.

In particular, the dye composition used in the process according to the invention is applied to wet or dry keratin fibres.

It is usually left in place on the fibres for a time generally of from 1 minute to 1 hour and preferably from 5 minutes to 30 minutes.

The temperature during the dyeing process conventionally ranges from room temperature (from 15° C. to 25° C.) to 80° C. and preferably from room temperature to 60° C.

After the treatment, the human keratin fibres are advantageously rinsed with water. They may optionally be washed with a shampoo, followed by rinsing with water, before being dried or left to dry.

The composition applied in the process according to the invention is generally prepared via extemporaneous mixing of at least two compositions, preferably two or three compositions.

In a first variant of the invention, the composition applied in the process according to the invention is derived from the extemporaneous mixing of two compositions.

In particular, a composition (A) (free of chemical oxidizing agent) comprising one or more oxidation bases, one or more meta-phenylenediamine-based couplers of formula (I) and one or more basifying agents is mixed with a composition (B) comprising one or more chemical oxidizing agents; at least one of the compositions (A) and (B) comprising one or more fatty substances and one or more surfactants, the fatty substance content of the composition according to the invention, resulting from the mixing of compositions (A) and (B) comprising at least 15% by weight of fatty substance.

At least one of the compositions (A) and (B) is advantageously aqueous.

The term "aqueous composition" means a composition comprising at least 5% by weight of water, relative to the weight of this composition.

Preferably, an aqueous composition comprises more than 10% by weight of water and even more advantageously more than 20% by weight of water.

Preferably, composition (A) is aqueous. Preferably, composition (B) is also aqueous.

In this variant, composition (A) preferably comprises at least 30% and better still at least 50% by weight of fatty substances and even more advantageously at least 30% and more particularly at least 50% by weight of fatty substances that are liquid at room temperature (25° C.), relative to the weight of this composition (A).

Preferably, composition (A) is a direct emulsion (oil-in-water: O/W) or an inverse emulsion (water-in-oil: W/O), and preferably a direct emulsion (O/W).

In this variant, compositions (A) and (B) are preferably mixed in an (A)/(B) weight ratio ranging from 0.2 to 10 and better still from 0.5 to 2.

In accordance with this first variant, the dyeing process according to the invention consists, in a first stage, in mixing composition (A) and composition (B) as defined previously just before application to the keratin fibres, and, in a second stage, in applying to the said keratin fibres the composition resulting from the mixing of compositions (A) and (B).

In a second variant of the invention, the composition used in the process according to the invention results from the extemporaneous mixing of three compositions. In particular, the three compositions are aqueous or alternatively at least one of them is anhydrous.

More particularly, within the meaning of the invention, the term "anhydrous cosmetic composition" means a cosmetic composition having a water content of less than 5% by weight, preferably of less than 2% by weight and even more preferably of less than 1% by weight, relative to the weight of the said composition. It should be noted that the water present in the composition is more particularly "bound water", such as the water of crystallization of the salts or traces of water absorbed by the raw materials used in the preparation of the compositions according to the invention.

Preferably, use is made of two aqueous compositions (B') and (C') and one anhydrous composition (A').

The anhydrous composition (A') (free of chemical oxidizing agent) then preferably comprises one or more fatty substances, and more preferentially one or more fatty substances that are liquid at room temperature and atmospheric pressure.

Composition (B') (free of chemical oxidizing agent) then preferably comprises one or more oxidation bases and one or more meta-phenylenediamine-based couplers of formula (I).

Composition (C') then preferably comprises one or more chemical oxidizing agents.

According to this preferred mode of the second variant, the basifying agent(s) are included in the compositions (A') and/or (B') and preferably only in composition (B'). As regards the surfactant(s), they are included in at least one of the compositions (A'), (B') and (C').

According to this preferred mode, the composition according to the invention, i.e. resulting from the extemporaneous mixing of the three compositions (A'), (B') and (C'), has a fatty substance content of at least 15% by weight, preferably at least 20% by weight and even more advantageously at least 25% by weight of fatty substance, relative to the weight of the composition resulting from mixing the three abovementioned compositions. According to a more preferably embodiment, the extemporaneous mixing of the three compositions (A'), (B') and (C') has a fatty substance content of at least 30% by weight, particularly at least 40% by weight and even more preferably at least 50% by weight of fatty substance, relative to the weight of the composition resulting from mixing the three abovementioned compositions.

In this variant, compositions (A'), (B') and (C') are preferably mixed together in a weight ratio [(A')+(B')]/(C') ranging from 0.2 to 10 and more particularly from 0.5 to 2 and in a weight ratio (A')/(B') ranging from 0.5 to 10 and preferably from 1 to 5.

In accordance with this second variant, the dyeing process according to the invention consists, in a first step, in mixing compositions (A'), (B') and (C') as defined previously just before application to the keratin fibres, and, in a second step, in applying to the said keratin fibres the composition resulting from the mixing of compositions (A'), (B') and (C').

Devices:

The invention relates to a first multi-compartment device comprising a first compartment containing composition (A) as described above and at least a second compartment containing composition (B) as described above; the compositions (A) and (B) of the compartments being intended to be mixed together before application to give a composition according to the invention; the amount of fatty substance of which represents at least 15% by weight, preferably at least 20% by weight and even more advantageously at least 25% by weight relative to the weight of the formulation resulting from the mixing of compositions (A) and (B). According to a preferably embodiment the amount of fatty substance represents at least 30% by weight, more particularly 40% by weight and even more advantageously at least 50% by weight relative to the weight of the formulation resulting from the mixing of compositions (A) and (B).

The invention also relates to a second multi-compartment device comprising a first compartment containing composition (A') as described above and a second compartment containing a cosmetic composition (B') as described above and at least a third compartment comprising composition (C') as described above, the compositions of the compartments being intended to be mixed together before application to give the composition according to the invention; the amount of fatty substance in the composition representing at least 15% by weight, preferably at least 20% by weight and even more advantageously at least 25% by weight relative to the weight of the composition according to the invention, i.e. resulting from the mixing of compositions (A'), (B') and (C'). According to a preferably embodiment the amount of fatty substance represents at least 30% by weight, more particularly 40% by weight and even more advantageously at least 50% by weigh relative to the weight of the composition according to the invention, i.e. resulting from the mixing of compositions (A'), (B') and (C').

The present invention also relates to the use of the dye composition as defined previously for dyeing keratin fibres, in particular human keratin fibres such as the hair.

The examples that follow serve to illustrate the invention without, however, being limiting in nature.

EXAMPLES

I. Protocol

Compositions (A) and (B) below are prepared from the ingredients indicated in the table below. The amounts mentioned are indicated in grams of active material.

Composition (A)

| Composition | A |
|---|---|
| 2-Octyldodecanol | 11.5 g |
| Liquid petroleum jelly | 75.5 g |
| Oxyethylenated lauryl alcohol (2 OE) | 3 g |
| Oxyethylenated sorbitan monolaurate (4 OE) | 11 g |

Composition (B)

| Composition | B |
|---|---|
| Monoethanolamine | 15.05 g |
| Sodium metabisulfite | 0.7 g |
| Ascorbic acid | 0.25 g |
| Diethylenetriaminepentaacetic acid | 1 g |
| Propylene glycol | 6.2 g |
| 96% ethanol | 8.8 g |
| Hexylene glycol | 3 g |
| Dipropylene glycol | 3 g |
| Oxidation base | $1.45 \times 10^{-2}$ mol |
| Coupler | $1.45 \times 10^{-2}$ mol |
| Water | qs 100 g |

Procedure

At the time of use, 0.828 ml of composition (A), 0.33 ml of composition (B) and 1.242 ml of a composition (C) of 20-volumes aqueous hydrogen peroxide solution are mixed together.

The mixture obtained is applied to 200 mg of locks of natural hair containing 90% white hairs. After a leave-on time of 30 minutes at room temperature, the locks are rinsed and then washed with a standard shampoo.

II. Calculation of the Colour Variation ($\Delta E_{ab}^*$)

The coloration build-up ($\Delta E_{ab}^*$) was evaluated in the CIE L* a* b* system. In this L* a* b* system, L* represents the intensity of the colour, a* indicates the green/red colour axis and b* indicates the blue/yellow colour axis. The lower the value of L*, the darker or more intense the colour.

The value of $\Delta E_{ab}^*$ was calculated from the values of L* a* b* according to equation (i) below:

$$\Delta E_{ab}^* = \sqrt{(L^*-L_o^*)^2+(a^*-a_o^*)^2(b^*-b_o^*)^2} \qquad (i)$$

The coloration build-up ($\Delta E_{Lab}^*$) was calculated on the locks of untreated hair ($L_0^*$, $a_0^*$ and $b_0^*$) and on locks of dyed hair (L*, a* and b*). The values of $L_0^*$, $a_0^*$ and $b_0^*$ for the untreated natural white hairs are, respectively, 55.56, 2.06 and 12.29.

The greater the value of $\Delta E_{ab}^*$, the better the coverage of the fibres.

IV. Results

| Coupler | Base | L | a | b | $\Delta E_{ab}^*$ |
|---|---|---|---|---|---|
| (structure: 2,6-diaminophenyl-S-CH2CH2-NH-C(O)-CH3) | (structure: 1,4-phenylenediamine) | 15.6 | −1.9 | −5.2 | 42.3 |

| Coupler | Base | L | a | b | ΔE$_{ab}$* |
|---|---|---|---|---|---|
| 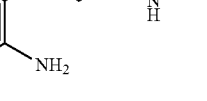 | 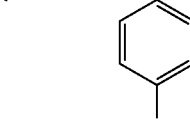 | 16.7 | −3.5 | −9.2 | 43.8 |
| 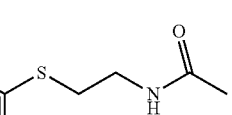 | 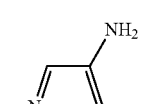 | 15 | 13.1 | −3.2 | 43.5 |
| Coupler | Base | L* | a* | b* | ΔE$_{ab}$* |
|---|---|---|---|---|---|
| 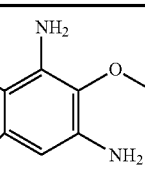 | 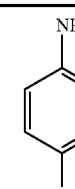 | 26.2 | 1.5 | 4.9 | 33.3 |
| 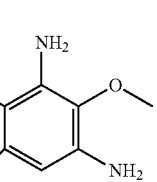 | 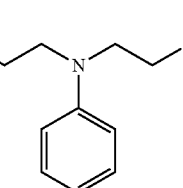 | 25.1 | −1.2 | 5.3 | 29.6 |
| 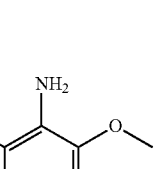 | 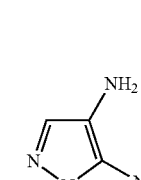 | 17.3 | 18.9 | 1.5 | 42 |

The build-ups of the dyes are significantly higher than that obtained with a standard oxidation dye support.

The invention claimed is:
1. Composition for dyeing keratin fibres, characterized in that it comprises:
   i) one or more fatty substances,
   ii) one or more surfactants,
   iii) one or more oxidation bases,
   iv) one or more basifying agents,
   v) one or more meta-phenylenediamine-based couplers of formula (I), and also the addition salts thereof, optical isomers, geometrical isomers and tautomers thereof, or solvates thereof:

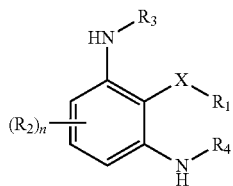

(I)

in which formula (I):
$R_1$ represents a linear or branched $C_1$-$C_6$ alkyl radical, which may be substituted with one or more of the following:
—$CONH_2$ radicals,
—$NHCOCH_3$ radicals,
—$NHSO_2CH_3$ radicals,
di($C_1$-$C_6$)alkylamino radicals,
hydroxyl radicals,
amino radicals,
—COOH radicals,
$R_2$ represents:
a hydrogen atom,
a linear or branched $C_1$-$C_6$ alkyl radical, which may be substituted with one or more of the following:
—$CONH_2$ radicals,
—$NHSO_2CH_3$ radicals,
di($C_1$-$C_6$)alkylamino radicals,
hydroxyl radicals,
amino radicals,
—COOH radicals,
$C_1$-$C_6$ alkoxy radicals,
a linear or branched $C_1$-$C_6$ alkoxy radical, which may be substituted with one or more of the following:
—$CONH_2$ radicals,
—$NHSO_2CH_3$ radicals,
di($C_1$-$C_6$)alkylamino radicals,
hydroxyl radicals,
amino radicals,
—COOH radicals,
$C_1$-$C_6$ alkoxy radicals,
a halogen radical,
$R_3$ and $R_4$ represent, independently of each other:
a hydrogen atom,
a linear or branched $C_1$-$C_6$ alkyl radical, which may be substituted with one or more of the following:
di($C_1$-$C_6$)alkylamino radicals,
hydroxyl radicals,
amino radicals,
$C_1$-$C_6$ alkoxy radicals, X represents an oxygen or sulfur atom,
n represents an integer ranging from 0 to 2,
(vi) one or more chemical oxidizing agents,
the fatty substance content representing in total at least 15% by weight relative to the total weight of the said dye composition.

2. Dye composition according to claim 1, characterized in that the fatty substance(s) are chosen from $C_6$-$C_{16}$ hydrocarbons, hydrocarbons containing more than 16 carbon atoms, non-silicone oils of animal origin, triglycerides of plant or synthetic origin, fluoro oils, fatty alcohols, fatty acid esters other than triglycerides and non-silicone waxes, fatty alcohol esters other than triglycerides and non-silicone waxes, non-silicone waxes, and silicones, and mixtures thereof.

3. Dye composition according to claim 1, characterized in that it comprises at least 20% by weight of fatty substance relative to the weight of the composition.

4. Dye composition according to claim 1, characterized in that the surfactants are chosen from nonionic surfactants.

5. Dye composition according to claim 1, characterized in that the oxidation bases are chosen from para-phenylenediamines, bis(phenyl)alkylenediamines, para-aminophenols, ortho-aminophenols, heterocyclic bases, and the addition salts thereof, and solvates thereof.

6. Dye composition according to claim 1, characterized in that the meta-phenylenediamine-based couplers are chosen from those of formula (I) in which $R_1$ represents a linear $C_1$-$C_4$ alkyl radical, optionally substituted with one or more hydroxyl groups, an amino group or a group —$NHCOCH_3$.

7. Dye composition according to claim 1, characterized in that the meta-phenylenediamine-based couplers are chosen from those of formula (I) in which $R_3$ and $R_4$ represent, independently of each other, a hydrogen atom or a linear $C_1$-$C_6$ alkyl radical, optionally substituted with a hydroxyl group.

8. Dye composition according to claim 1, characterized in that the meta-phenylenediamine-based couplers of formula (I) are chosen from the following compounds, the addition salts thereof, optical isomers, geometrical isomers and tautomers thereof, and solvates thereof:

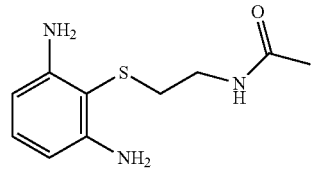

(1)

N-[2-(2,6-diaminophenylsulfanyl)ethyl]acetamide

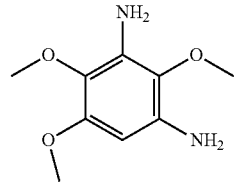

(2)

2,4,5-trimethoxybenzene-1,3-diamine

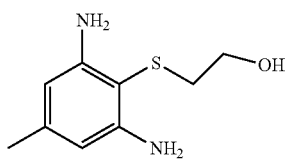
2-(2,6-diamino-4-methylphenylsulfanyl)ethanol
(3)

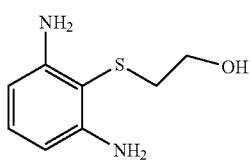
2-(2,6-diaminophenylsulfanyl)ethanol
(4)

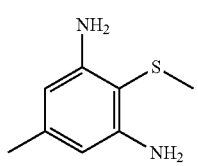
5-methyl-2-methylsulfanyl-benzene-1,3-diamine
(5)

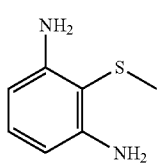
2-methylsulfanyl-benzene-1,3-diamine
(6)

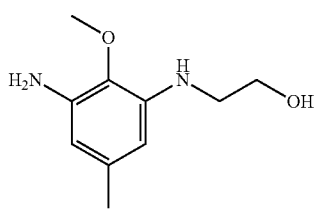
2-(3-amino-2-methoxy-5-methylphenylamino)ethanol
(7)

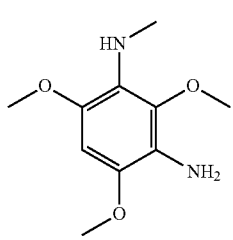
2,4,6-trimethoxy-N-methyl-benzene-1,3-diamine
(8)

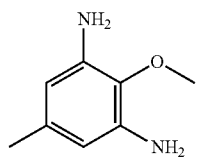
2-methoxy-5-methyl-benzene-1,3-diamine
(9)

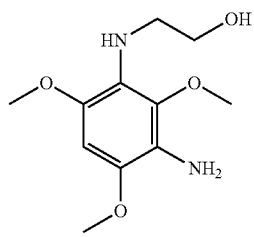
2-(3-amino-2,4,6-trimethoxyphenylamino)ethanol
(10)

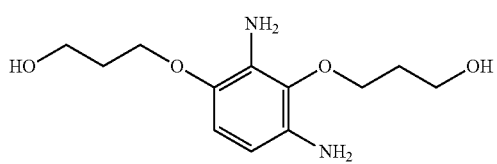
3-[2,6-diamino-3-(3-hydroxypropoxy)phenoxy]propan-1-ol
(11)

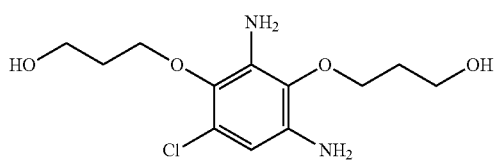
3-[2,6-diamino-4-chloro-3-(3-hydroxypropoxy)phenoxy]propan-1-ol
(12)

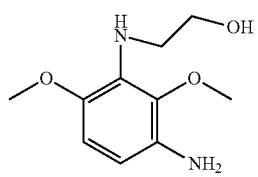
2-(3-amino-2,6-dimethoxyphenylamino)ethanol
(13)

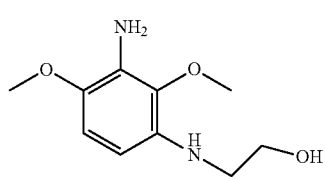
2-(3-amino-2,4-dimethoxyphenylamino)ethanol
(14)

-continued

(15)
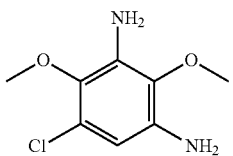
5-chloro-2,4-dimethoxy-benzene-1,3-diamine

(21)
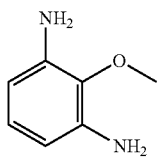
2-methoxybenzene-1,3-diamine

(16)
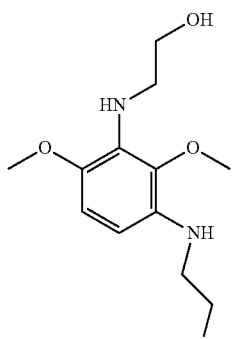
2-[3-(2-hydroxyethylamino)-2,6-dimethoxyphenylamino]ethanol

(17)
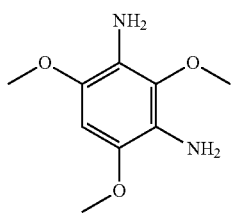
2,4,6-trimethoxybenzene-1,3-diamine

(18)
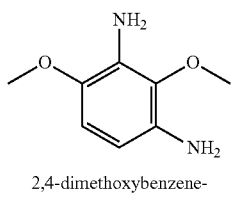
2,4-dimethoxybenzene-1,3-diamine

(19)
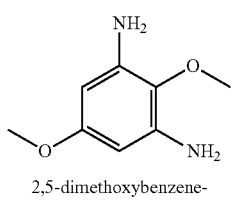
2,5-dimethoxybenzene-1,3-diamine

(20)
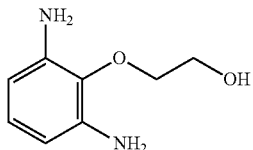
2-(2,6-diaminophenoxy)ethanol

9. Dye composition according to claim 1, characterized in that coupler(s) are chosen from couplers (1) and (2), and also the addition salts thereof, optical isomers, geometrical isomers and tautomers thereof, and solvates thereof.

10. Dye composition according to claim 1, characterized in that the basifying agent(s) are mineral, organic or hybrid, chosen from aqueous ammonia, alkali metal carbonates or bicarbonates, sodium hydroxide, potassium hydroxide, organic amines chosen from alkanolamines, oxyethylenated and/or oxypropylenated ethylenediamines, amino acids and the compounds of formula (II) and mixtures thereof:

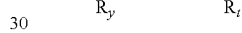

(II)

in which formula (II) W is a divalent $C_1$-$C_6$ alkylene radical optionally substituted with one or more hydroxyl groups or a $C_1$-$C_6$ alkyl radical, optionally interrupted with one or more heteroatoms such as O, or $NR_u$, $R_x$, $R_y$, $R_z$, $R_t$ and $R_u$, which may be identical or different, represent a hydrogen atom or a $C_1$-$C_6$ alkyl, $C_1$-$C_6$ hydroxyalkyl or $C_1$-$C_6$ aminoalkyl radical.

11. Dye composition according to claim 1, characterized in that the basifying agents are chosen from alkanolamines and amino acids in neutral or ionic form.

12. Dye composition according to claim 1, characterized in that it comprises at least hydrogen peroxide as chemical oxidizing agent.

13. Process for dyeing keratin fibres, which consists in applying to the said fibres a dye composition as defined according to claim 1.

14. Dyeing process according to claim 13, characterized in that the composition results from the extemporaneous mixing of two compositions; a composition (A) comprising one or more oxidation bases, one or more meta-phenylenediamine-based couplers of formula (I) and one or more basifying agents, and a composition (B) comprising one or more chemical oxidizing agents, at least one of the compositions (A) and (B) comprising one or more fatty substances and one or more surfactants; the fatty substance content of the composition resulting from the extemporaneous mixing of compositions (A) and (B) corresponding to at least 15% by weight of fatty substance.

15. Process according to claim 14, characterized in that the composition results from the extemporaneous mixing of three compositions; two aqueous compositions (B') and (C') and an anhydrous composition (A'), the anhydrous composition (A') comprising one or more fatty substances, the composition (B') comprising one or more oxidation bases and one or more meta-phenylenediamine-based couplers of formula (I), the composition (C') comprising one or more chemical oxidizing agents, one or more basifying agents being included in the compositions (A') and/or (B') and preferably only in composition (B'), one or more surfactants being included in at least one of the compositions (A'), (B') and (C'), the fatty substance content of the composition resulting from the extemporaneous mixing of the three compositions (A'), (B') and (C') representing at least 15% by weight of fatty substance.

16. Multi-compartment device comprising a first compartment containing composition (A) as described in claim 14 and at least a second compartment containing composition (B) as described in claim 14, the compositions of the compartments being intended to be mixed together before application, on condition that the amount of fatty substance represents at least 15% by weight relative to the weight of the composition resulting from the mixing of (A) and (B).

17. Multi-compartment device comprising a first compartment containing composition (A') as described in claim 15; and a second compartment containing a cosmetic composition (B') as described in claim 15 and at least a third compartment comprising composition (C') as described in claim 15; the compositions of the compartments being intended to be mixed together before application, on condition that the amount of fatty substance represents at least 15% by weight relative to the weight of the composition resulting from the mixing of (A'), (B') and (C').

18. Dye composition according to claim 2, characterized in that the fatty substance(s) are chosen from liquid petroleum jelly, $C_6$-$C_{16}$ alkanes, polydecenes, liquid esters of fatty acids other than triglycerides, liquid esters of fatty alcohols other than triglycerides, and liquid fatty alcohols, and mixtures thereof.

19. Dye composition according to claim 4, characterized in that the nonionic surfactants are chosen from monooxyalkylenated or polyoxyalkylenated nonionic surfactants, monoglycerolated or polyglycerolated nonionic surfactants, and alkylpolyglucosides, and mixtures thereof.

20. Dye composition according to claim 6, characterized in that the meta-phenylenediamine-based couplers are chosen from those of formula (I) in which $R_1$ represents a $C_1$ alkyl radical, optionally substituted with one or more hydroxyl groups, an amino group or a group —$NHCOCH_3$.

* * * * *

UNITED STATES PATENT AND TRADEMARK OFFICE
CERTIFICATE OF CORRECTION

PATENT NO. : 9,585,824 B2
APPLICATION NO. : 14/764530
DATED : March 7, 2017
INVENTOR(S) : S. Sabelle It is certified that error appears in the above-identified patent and that said Letters Patent is hereby corrected as shown below:

| Column | Line | Error |
|---|---|---|
| 44 (Claim 10, Line 7) | 22 | "(II) and" should read --(II), and-- |
| 44 (Claim 14, Line 3) | 50 | "compositions;" should read --compositions:-- |
| 44 (Claim 15, Line 3) | 62 | "compositions;" should read --compositions:-- |
| 45 (Claim 15, Line 11) | 3 | "preferably only" should read --only-- |

Signed and Sealed this
Sixth Day of March, 2018

Andrei Iancu
*Director of the United States Patent and Trademark Office*